US008703420B2

(12) United States Patent
Garaizar Candina et al.

(10) Patent No.: US 8,703,420 B2
(45) Date of Patent: Apr. 22, 2014

(54) **METHODS AND REAGENTS FOR THE DETECTION OF *SALMONELLA* SPP**

(75) Inventors: Javier Garaizar Candina, Leioa (ES); Aitor Rementeria Ruiz, Leioa (ES); Joseba Bikandi Bikandi, Leioa (ES); Fernando Lopitz Otsoa, Leioa (ES); Ilargi Martinez Ballesteros, Leioa (ES); Fernando Perez Aguirre, Obdullo Lopez de Uralde (ES); Isabel Santaolalla Ruiz De Galarreta, Obdulio Lopez de Uralde (ES)

(73) Assignee: Universidad del Pais Vasco, Leioa-Vizcaya (ES)

( * ) Notice: Subject to any disclaimer, the term of this patent is extended or adjusted under 35 U.S.C. 154(b) by 77 days.

(21) Appl. No.: 12/990,532

(22) PCT Filed: Apr. 28, 2009

(86) PCT No.: PCT/ES2009/070121
§ 371 (c)(1),
(2), (4) Date: Feb. 1, 2011

(87) PCT Pub. No.: WO2009/133226
PCT Pub. Date: Nov. 5, 2009

(65) Prior Publication Data
US 2011/0151458 A1 Jun. 23, 2011

(30) Foreign Application Priority Data
Apr. 30, 2008 (ES) .................................. 200801267

(51) Int. Cl.
*C12Q 1/68* (2006.01)
*C07H 21/04* (2006.01)

(52) U.S. Cl.
USPC .... 435/6.12; 435/6.15; 536/24.32; 536/24.33

(58) Field of Classification Search
None
See application file for complete search history.

(56) References Cited

U.S. PATENT DOCUMENTS

| 6,060,240 A * | 5/2000 | Kamb et al. ...................... 506/4 |
| 6,893,847 B2 | 5/2005 | Yokoyama et al. |
| 2003/0118998 A1* | 6/2003 | Dean et al. ........................ 435/6 |

FOREIGN PATENT DOCUMENTS

| EP | 0739987 A2 | 10/1995 |
| EP | 1233073 A2 | 8/2002 |
| WO | WO-2004046375 A2 | 6/2004 |

OTHER PUBLICATIONS

Cortez et al. Research in Veterinary Science (2006) 81: 340-344.*
Lowe et al. Nucleic Acids Research (1990) 18(7): 1757-1761.*
GenBank Accession No. U43250 for the invA gene of *Salmonella enterica*, Mar. 21, 1997 [online], [retrieved on Mar. 18, 2012], retrieved from the Internet: <URL: www.ncbi.nlm.nih.gov/nuccore/u43250>.*
Wittwer et al. BioTechniques (1997) 22(1): 130-131 & 134-138.*
Galan, J.E. et al., Molecular and Functional Characterization of the *Salmonella* Invasion Gene InvA: Homology of InvA to members of a New Protein Family, *Journal of Bacteriology*, (1992), vol. 174 (13), pp. 4338-4339.
Fidelma Boyd, E. et al, Comparative Genetics in the Inv-Spa Invasion Gene Complex of *Salmonella enterica*, *Journal of Bacteriology*, (2007), vol. 179(6), pp. 1985-1991.
Alvarez, J., et. al., Development of a Multiplex PCR Technique for Detection and Epidemiological Typing of *Salmonella* in Human Clinical Samples, *Journal of Clinical Microbiology*, (2004), vol. 42(4), pp. 1734-1738.
Rahn, K., at al., Amplification of an invA gene sequence of *Salmnella typhimurium* by poly merase chanin reaction as a specific method of detection of *Salmonella*, Molecular and Cellular Probes, *Academic Prss*, London, GB LNKD-DOI:10.1016/0890-8508(92) 90002-F, (1992), vol. 6(4), pp. 271-279.
Fey, A. et al., Establishment of a Real-Time PCR-Based Approach for Accurate Quantification of Bacterial RNA Targets in Water, Using *Salmonella* as a Model Organism, *Applided and Environmental Microbiology*, (Jun. 2004), vol. 70(6), pp. 3618-3623.
Fukushima, H. et al., Duplex Real-Time SYBR Green PCR Assays for Detection of 17 Species of Food- or Waterborne Pthogens in Stools, *Journal of Clinical Microbiology*, (2003), vol. 41(11), pp. 5134-5146.
Nam, H. et al., Application of SYBR green real-time PCR assay for Specific Detection of *Salmonella* spp. in dairy farm environmental samples, *International Journal of Food Microbiology*, (2005), vol. 102, pp. 151-171.

* cited by examiner

*Primary Examiner* — Angela M Bertagna
(74) *Attorney, Agent, or Firm* — Blue Filament Law PLLC; Avery N. Goldstein

(57) ABSTRACT

The invention relates to an in vitro method for the detection of bacteria of the *Salmonella* spp. genus by means of a quantitative polymerase chain reaction using specific primers for the pathogen from DNA and RNA samples from the microorganism. The method is useful in the detection of viable and non-viable microorganisms of *Salmonella* spp. in environmental, clinical and food samples. Likewise, the invention also relates to a kit used for putting the method into practice.

13 Claims, 2 Drawing Sheets

METHODS AND REAGENTS FOR THE DETECTION OF *SALMONELLA* SPP

CROSS-REFERENCE TO RELATED APPLICATIONS

This application is the U.S. national phase of PCT/ES2009/070121 filed Apr. 28, 2009, which claims priority of Spanish Patent Application No. P200801267 filed Apr. 30, 2008.

FIELD OF THE INVENTION

The invention relates to an in vitro method for the detection of bacteria of the *Salmonella* spp. genus by means of a quantitative polymerase chain reaction using specific primers for said pathogen from DNA and RNA samples from said microorganism. Said method is useful in the detection of viable and non-viable microorganisms of *Salmonella* spp. in environmental, clinical and food samples. Likewise, the invention also relates to a kit for putting said method into practice.

BACKGROUND

*Salmonellosis* is one of the most common and wide spread food diseases caused by bacteria of the *Salmonella* spp. genus. It has been estimated that *Salmonella* spp. is responsible for more than 1.4 million cases of enterocolitis and more than 500 deaths per year in the United States.

The current taxonomic system of *Salmonella* spp. has regrouped all the strains of *Salmonella* spp. (pathogenic or not) into two single species: *S. enterica* and *S. bongori*. The latter (previously subspecies V) does not seem to be pathogenic for human beings.

*S. enterica* species has six subspecies (sometimes as subgroups under Roman numerals): *enterica* (I); *salamae* (II); *arizonae* (IIIa); *diarizonae* (IIIb); *houtenae* (IV); *S. bongori* (V), already included in a different species; and *indica* (VI).

Each subspecies is in turn formed by different serotypes, up until now more than 2,500 being identified. One of them is *S. enterica* subsp. *enterica* (or subgroup I) which is divided into five serogroups: A, B, C, D and E. Each serogroup in turn comprises multiple components, giving rise to serovars (serotypes).

With clinical epidemiological importance, the more than 2500 serovars of *Salmonella* spp. can be grouped into three ecological divisions (spp. are subspecies):
1. *Salmonella* spp. adapted to live in human beings, among them, *S. Typhi*, *S. Paratyphi* A, B and C;
2. *Salmonella* spp. adapted to non-human hosts, which circumstantially can cause infections in humans, among them, *S. Dublin* and *S. Choleraesuis*;
3. *Salmonella* spp. without specific host adaptation, which includes 1,800 serovars widely distributed in nature, which cause most cases of salmonellosis worldwide.

The typical detection of this pathogen includes procedures based on the culture and biochemical identification of colonies. The standard operating procedure based on the culture requires seven days to confirm the presence of this pathogen in the sample analyzed. Although these procedures are efficient, they are too slow to be used systematically in a large number of samples.

As an alternative to the procedures based on the culture and biochemical identification of the colonies of *Salmonella* spp., there are a number of techniques for the detection of said pathogen based on PCR (polymerase chain reaction) technology. Furthermore, by means of said technology it is also possible to detect live cells if starting from RNA to perform PCR or live and dead cells if starting from genomic DNA.

U.S. Pat. No. 6,893,847 describes oligonucleotides especially designed for detecting mRNA of the *Salmonella* spp. invA gene.

Fey et al. (*Applied and Environmental Microbiology*, 2004 vol. 70(6): 3618-3623) have developed a method for the detection of bacterial RNA in water sample based on the use of real time PCR. To test the developed method, invA gene and 16S rRNA of *Salmonella enterica* serovar *Typhimurium* are used.

Fukushima, H. et al. (Journal of Clinical Microbiology, 2003, vol. 41(11): 5134-5146) describe a Duplex Real Time PCR assay using SYBR Green for the detection of 17 species of pathogens present in water and food starting from genomic DNA. *Salmonella* spp. is among the pathogenic species detected. Primers targeted at amplifying the *Samonella* spp. invA gene are used for its detection.

Furthermore, methods allowing the detection of multiple *Salmonella* spp. species and serovars have also been developed in the state of the art by means of a single PCR reaction:

Nam, H. et al. (International Journal of Food Microbiology, 2005, vol. 102: 161-171) describe a Real Time PCR assay using SYBR Green for the detection of different *Salmonella* spp. species (see Table 1 of said publication) starting from DNA. To that end they have designed a pair of primers which specifically amplifies a 119 by fragment of the *Salmonella* invA gene.

Patent application EP0739987 describes a method for the detection of different *Salmonella* spp. species from DNA by means of a PCR comprising the use of oligonucleotides specifically targeted at the *Salmonella* spp. invA gene.

Rahn et al. (Molecular and Cellular probes, 1992 vol. 6: 271-279) describe a method for the detection of multiple *Salmonella* spp. species from DNA comprising the amplification of the sequence of the *Salmonella* spp. invA gene by means of a polymerase chain reaction.

Therefore, there is in the state of the art a need to develop a method for the detection of *Salmonella* spp. which allows detecting a large number of serovars of said pathogen and which is in turn efficient, fast and cost-effective.

SUMMARY OF THE INVENTION

In one aspect the invention relates to an in vitro method for the detection of *Salmonella* spp. in a sample comprising
  (i) performing an amplification reaction from a nucleic acid preparation derived from said sample using a pair of primers capable of amplifying a region of the *Salmonella* spp. invA gene comprising the region of said gene corresponding to the region comprised between nucleotides 1001 and 1069 in the nucleotide sequence shown in SEQ ID NO: 1, and
  (ii) detecting the product of amplification generated in step (i).

In another aspect the invention relates to an in vitro method for the detection of *Salmonella* spp. in a sample comprising
  (i) performing an amplification reaction from a nucleic acid preparation derived from said sample using a pair of primers comprising the SEQ ID NO: 5 and SEQ ID NO: 6 sequences [INVAVITONE F/R]; and
  (ii) detecting the product of amplification by means of using a labeled probe, wherein said probe comprises a reporter pigment at its 5' end and a quencher pigment at its 3' end and has the nucleotide sequence shown in SEQ ID NO: 7 [INVAVITONE].

In another aspect the invention relates to an oligonucleotide the sequence of which is selected from the group of SEQ ID NO: 2 [INVAVITWO F primer], SEQ ID NO: 3 [INVAVITWO R primer], SEQ ID NO: 4 [INVAVITWO probe], SEQ ID NO: 7 [INVAVITONE probe] sequences.

In another aspect the invention relates to a kit comprising a pair of primers capable of amplifying a region of the *Salmonella* spp. invA gene comprising the region of said gene corresponding to the region comprised between nucleotides 1001 and 1069 in the nucleotide sequence shown in SEQ ID NO: 1.

In another aspect the invention relates to a kit comprising (i) the pair of SEQ ID NO: 5/SEQ ID NO: 6 primers [INVAVITONE F/R] and (ii) a labeled probe, wherein said probe comprises a reporter pigment at its 5' end and a quencher pigment at its 3' end and has the nucleotide sequence shown in SEQ ID NO: 7 [INVAVITONE].

Finally, the use of the kits of the invention in the detection of *Salmonella* spp. constitutes aspects included within the context of the present invention.

Thus, in one aspect the invention relates to the use of a kit according to what has been described in the present invention for the detection of *Salmonella* spp. in a sample.

DESCRIPTION OF THE INVENTION

Figure 1:
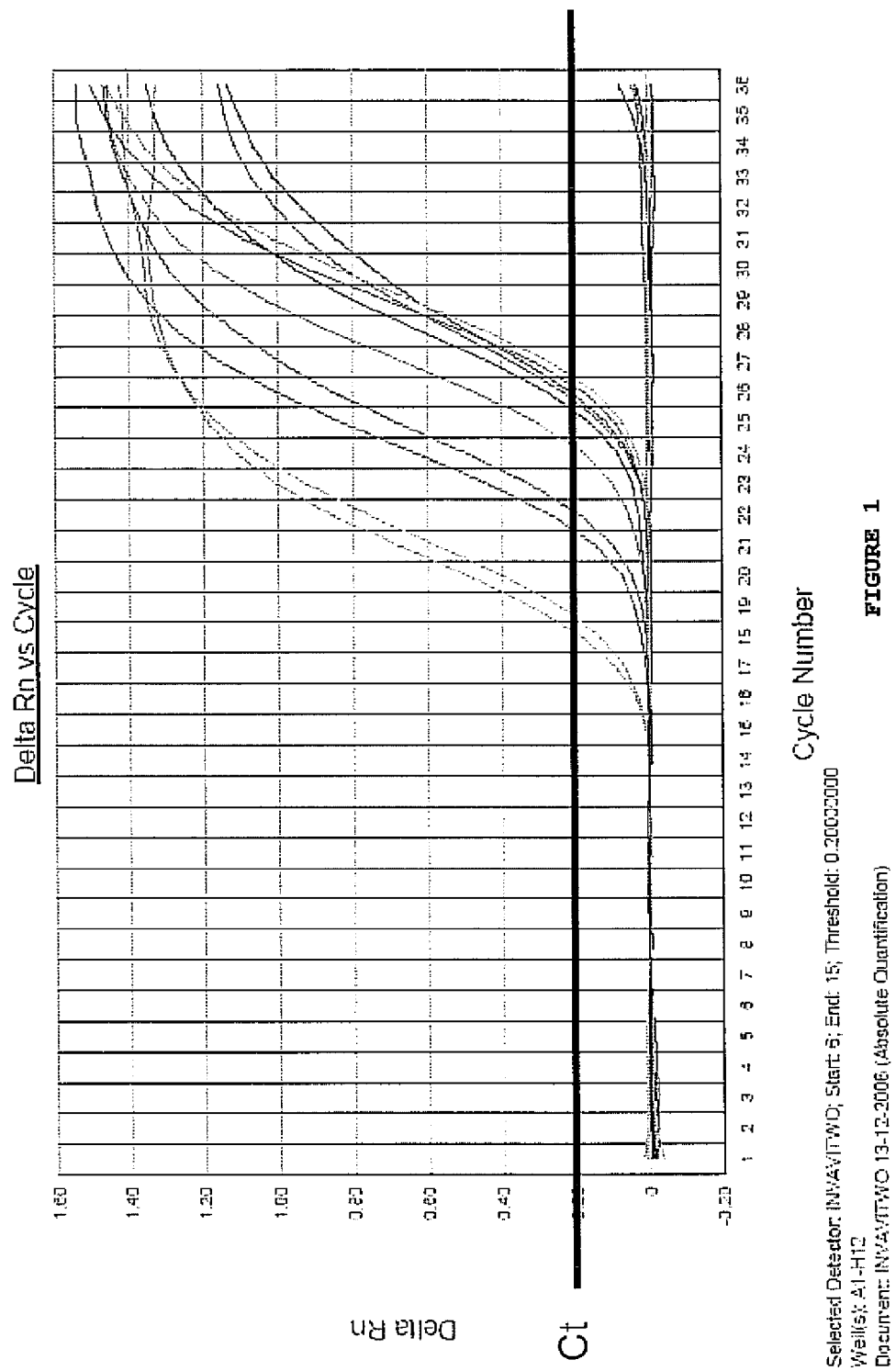
FIG. 1 is a graph showing the results of amplification of the *Salmonella* genome by RT-PCR in the samples analyzed. The lines in which values higher than Ct are observed correspond to different *Salmonella* strains. The lines in which values less than Ct are observed correspond to strains of genera different from *Salmonella*.

Investigators have surprisingly designed pairs of primers which allow the specific detection of microorganisms of the *Salmonella* spp. genus due to the fact that they amplify a region of the *Salmonella* spp. genome which is very conserved among all the species of the genus, and even at the variant level, which allows the detection of multiple *Salmonella* spp. species and serovars with a single assay.

Thus, in one aspect the invention relates to an in vitro method for the detection of *Salmonella* spp. in a sample (method 1 of the invention) comprising
  (i) performing an amplification reaction from a nucleic acid preparation derived from said sample using a pair of primers capable of amplifying a region of the *Salmonella* spp. invA gene comprising the region of said gene corresponding to the region comprised between nucleotides 1001 and 1069 in the nucleotide sequence shown in SEQ ID NO: 1, and
  (ii) detecting the product of amplification generated in step (i).

In the present invention, "nucleic acid" is understood as the repetition of monomers referred to as nucleotides, bound by means of phosphodiester bonds. There are two types of nucleic acids: DNA (deoxyribonucleic acid) and RNA (ribonucleic acid). Additionally, complementary DNA (cDNA) which is also considered a nucleic acid can be artificially obtained from RNA.

Therefore, in the present invention "nucleic acid preparation" is understood as the set of nucleic acids, i.e., DNA and/or cDNA, derived from the reverse transcription of the RNA present in a preparation which will be subjected to an amplification reaction.

In the present invention, "DNA" or "genomic DNA" is understood as the genetic material of live organisms controlling heredity and it is located in the nucleus of cells.

In the present invention, "RNA" is understood as the molecule resulting from the transcription of a DNA sequence.

In the present invention, "cDNA" is understood as the DNA obtained from the mRNA by action of reverse transcriptase.

As understood by the person skilled in the art, the detection of *Salmonella* spp. from RNA involves the existence of viable *Salmonella* spp. cells in the analyzed sample. Therefore, putting the method of the invention into practice allows not only detecting *Salmonella* spp. (if the starting sample is a genomic DNA preparation), but rather exclusively detecting viable *Salmonella* spp. cells present in the analyzed sample (if the starting sample is a cDNA preparation obtained from an RNA preparation of *Salmonella* spp.).

The method of the invention requires extracting nucleic acid from a sample. Different techniques for extracting nucleic acids are widely known in the state of the art, for example, penetrability chromatography, ion exchange chromatography, adsorption chromatography, ultrafiltration, use of magnetic beads to which the nucleic acids are selectively bound, etc. (Sambrook et al., 2001. "Molecular cloning: a Laboratory Manual", 3rd ed., Cold Spring Harbor Laboratory Press, N.Y., Vol. 1-3). Additionally, there are commercially available nucleic acid extraction kits for performing said extraction.

If the nucleic acid is DNA, the extraction can be performed by means of using chelating resins (e.g. CHELEX 100) and ion exchange, for example. These resins can be natural (aluminosilicates) such as zeolites, mineral clays and feldspars. Or they can be synthetic, such as hydrated metal oxides (hydrated titanium oxide), insoluble polyvalent metal salts (titanium phosphate), insoluble heteropolysaccharide salts (ammonium molybdophosphate), complex salts based on insoluble hexacyanoferrates and synthetic zeolites. These resins have a high affinity for polyvalent metal ions and are used to overcome PCR inhibitors present in the DNA of the sample.

In the event that the nucleic acid which is to be extracted from the sample is RNA, there are commercial kits exclusively designed for this purpose containing the components suitable for extracting the RNA in perfect conditions: high concentrations of chaotropic salts in the lysis buffer to inactivate the RNases, silica membranes favoring the adsorption of RNA, DNases eliminating DNA to achieve an RNA isolate of great purity, etc. A commercial kit having the aforementioned features includes but is not limited to Nucleospin® RNA, for example.

The method of the invention comprises an amplification reaction from a nucleic acid preparation. As understood by the person skilled in the art, an amplification reaction basically consists of the exponential multiplication of a target DNA molecule (or of a target region of a DNA molecule) by means of using oligonucleotides which hybridize with the regions flanking the target region to be amplified. The different techniques or processes for carrying out amplification reactions are widely described in the state of the art, for example in Sambrook et al., 2001. (see above). Examples of amplification reactions include but are not limited to polymerase chain reaction (PCR) and variations thereof [Regional Amplification PCR (RA-PCR), Real Time PCR (RT-PCR), etc.]. The protocol followed for carrying out PCR is widely known in the state of the art and there are currently commercial kits containing the materials necessary for carrying out said amplification. Likewise, the temperature conditions, time, reagent concentrations and number of PCR cycles will depend on the DNA polymerase used in the amplification reaction, on the specificity of the primers, etc. If a commercial kit is used, the reaction conditions will be those specified by the kit manufacturer.

Thus, in a particular embodiment of the invention, the amplification reaction is carried out by means of a real time polymerase chain reaction. A real time PCR is basically a conventional PCR in which the amplification equipment (thermocyclers) are provided with a fluorescence detection system, said detection being based on the use of specific molecules referred to as fluorophores and quenchers.

Figure 2:
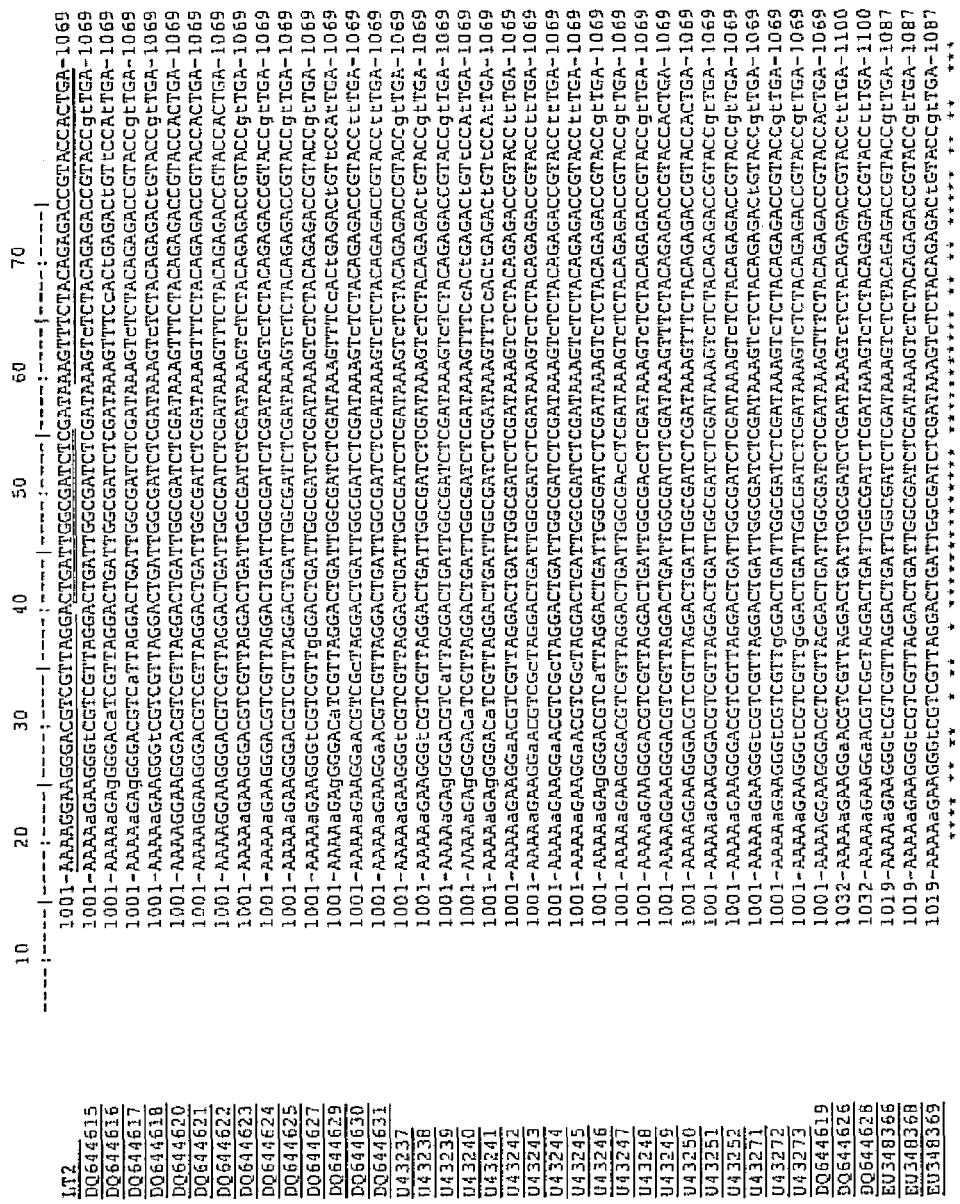
FIG. 2 is a multiple sequence alignment. The aligned sequences correspond to the *Salmonella* spp. invA gene, in which the sequence shown under the "LT2" indication is the nucleotide sequence comprising the region comprised between nucleotides 1001 and 1069 in the nucleotide sequence shown in SEQ ID NO: 1. The sequence indicated with a single underline corresponds to the nucleotide sequence of the INVAVITWO-F and INVAVITWO-R primers; the sequence indicated with a double underline corresponds to the nucleotide sequence of the INVAVITWO probe. The remaining sequences in the alignment correspond to the following *Salmonella* spp. species (the access number of the EMBL nucleotide sequence database is in bold print): DQ644615: *Salmonella enterica* subsp. *Enterica* strain CNM-3685-03 (SEQ. ID. NO. 16); DQ644616: *Salmonella enterica* subsp. *Salamae* strain CNM-5936-02 (SEQ. ID. NO. 17); DQ644617: *Salmonella enterica* subsp. *Salamae* strain CNM-176 (SEQ. ID. NO. 18); DQ644618: *Salmonella enterica* subsp. *Salamae* strain CNM-169 (SEQ. ID. NO. 19); DQ644620: *Salmonella enterica* subsp. *Arizonae* strain CNM-771-03 (SEQ ID. NO. 20); DQ644621: *Salmonella enterica* subsp. *Arizonae* strain CNM-247 (SEQ ID. NO. 21); DQ644622: *Salmonella enterica* subsp. *Arizonae* strain CNM-259 (SEQ ID. NO. 22); DQ644623: *Salmonella enterica* subsp. *Diarizonae* strain CNM-834-02 (SEQ. ID. NO. 23); DQ644624: *Salmonella enterica* subsp. *Diarizonae* strain CNM-750-02 (SEQ ID. NO. 24); DQ644625: *Salmonella enterica* subsp. *Diarizonae* strain CNM-2667-02 (SEQ ID. NO. 25); DQ644627: *Salmonella enterica* subsp. *Houtenae* strain ST-22 (SEQ ID. NO. 26); DQ644629: *Salmonella enterica* subsp. *Indica* strain CNM-186 (SEQ ID. NO. 27); DQ644630: *Salmonella enterica* subsp. *Indica* strain CDC-811 (SEQ ID. NO. 28); DQ644631: *Salmonella enterica* subsp. *Indica* strain CDC-1937 (SEQ ID. NO. 29); U43237: *Salmonella enterica* strain RKS4194 (SEQ ID. NO. 30); U43238: *Salmonella enterica* strain RKS3333 (SEQ ID. NO. 31); U43239: *Salmonella enterica* strain RKS3057 (SEQ ID. NO. 32); U43240: *Salmonella enterica* strain RKS3044 (SEQ ID. NO. 33); U43241: *Salmonella enterica* strain RKS3041 (SEQ ID. NO. 34); U43242: *Salmonella enterica* invasion strain RKS3027 (SEQ ID. NO. 35); U43243: *Salmonella enterica* strain RKS3015 (SEQ ID. NO. 36); U43244: *Salmonella enterica* strain RKS3014 (SEQ ID. NO. 37); U43245: *Salmonella enterica* strain RKS3013 (SEQ ID. NO. 38); U43246: *Salmonella enterica* strain RKS2995 (SEQ ID. NO. 39); U43247: *Salmonella enterica* strain RKS2993 (SEQ ID. NO. 40); U43248: *Salmonella enterica* strain RKS2985 (SEQ ID. NO. 41); U43249: *Salmonella enterica* strain RKS2983 (SEQ ID. NO. 42); U43250: *Salmonella enterica* strain RKS2980 (SEQ ID. NO. 43); U43251: *Salmonella enterica* strain RK52979 (SEQ ID. NO. 44); U43252: *Salmonella enterica* strain RKS2978 (SEQ ID. NO. 45); U43271: *Salmonella enterica* strain RKS1280 (SEQ ID. NO. 46); U43272: *Salmonella enterica* strain RKS1518 (SEQ ID. NO. 47); U43273: *Salmonella gallinarum* strain RKS2962 (SEQ ID. NO. 48); DQ644619: *Salmonella enterica* subsp. *Arizonae* strain CNM-822-02 (SEQ ID. NO. 49); DQ644626: *Salmonella enterica* subsp. *Houtenae* strain CNM-2556-03 (SEQ ID. NO. 50); DQ644628: *Salmonella enterica* subsp. *Houtenae* strain ST-15 (SEQ ID. NO. 51); EU348366: *Salmonella enterica* subsp. *Enterica* serovar Gallinarum strain S9873 (SEQ ID. NO. 52); EU348368: *Salmonella enterica* subsp. *Enterica* serovar Pullorum strain 1794 (SEQ ID. NO. 53); EU348369: *Salmonella enterica* subsp. *Enterica* serovar Senftenberg strain JXS-04#01 (SEQ ID. NO. 54). The nucleotides in uppercase letters indicate a nucleotide match among the compared sequences the nucleotides in lowercase letters indicate no match among the compared sequences. At the end of the alignment, the consensus sequence among all the compared sequences is shown by means of asterisks.

As understood by the person skilled in the art, an amplification reaction requires the use of a pair of oligonucleotides, referred to as primers, which will hybridize with the target region/sequence which is to be amplified. In the specific case of the present method, the target region to be amplified is a region of the *Salmonella* spp. invA gene comprising the region of said gene corresponding to the region comprised between nucleotides 1001 and 1069 in the nucleotide sequence shown in SEQ ID NO: 1. FIG. 2 attached to the present description shows the region of the invA gene of different *Salmonella* spp. species corresponding to the region comprised between nucleotides 1001 and 1069 in the nucleotide sequence shown in SEQ ID NO: 1. As understood by the person skilled in the art, all the sequences shown in FIG. 2 are homologous sequences (which share a consensus sequence) which will be detected upon putting the method of the invention into practice, thus allowing the detection of the different *Salmonella* spp. species/serovars. Likewise, the person skilled in the art will note that the method of the invention is suitable for the detection of other *Salmonella* species and strains not indicated in FIG. 2 provided that the region of the invA gene corresponding to the region indicated in said figure shows a substantial sequence similarity with the consensus sequence predicted from said alignment and, in particular, with the central region thereof with respect to which the hybridization probe is targeted. In a particular embodiment of the invention, the pair of primers used in the amplification reaction for amplifying said target region comprises the SEQ ID NO: 2 and 3 sequences [INVAVITWO F/R].

Additionally, the amplification reaction can be carried out using an amplification system which allows eliminating contamination with amplified products derived from previous amplification cycles. This is the case of the AmpErase® uracil-N-glycosylase amplification master, for example, as is shown in the example attached to the present description (chapter B, point 2). Uracil-N-glycosylase is an enzyme which degrades the DNA incorporating dUTPs instead of dTTPs of the "natural DNA". The occurrence of false positives due to the mentioned contamination is thus prevented.

Once the amplification reaction is carried out it is necessary to detect the products of amplification or amplicons. Again, the techniques for detecting the products of amplification are widely described in the state of the art, such as in Sambrook et al., 2001. (mentioned above), for example. Any of the amplification fragment identification procedures known in the state of the art can be used in said detection, such as hybridization with labeled probes (with a fluorophore, for example), staining, for example, silver staining, with intercalating agents, such as ethidium bromide or SYBR Green®, etc.

As is known of the state of the art, if the chosen amplification method is a real time PCR, the detection of the product of amplification is carried out simultaneously to the amplification reaction. To that end, both specific and non-specific detection mechanisms can be used.

Non-specific detection mechanisms detect all double-stranded DNA produced during the amplification reaction (either a specific product, an non-specific product or primer dimers). This mechanism is the standard method and basically consists of adding a double-stranded intercalating agent or a fluorescence-emitting fluorophore when it binds to it. Agents suitable for this purpose include SYTO 15, SYTO 25, SYTO 13, SYTO 9, SYBR Green I, SYTO 16, SYTO 17, SYTO 17, SYTO 21, SYTO 59, SYTO 16, SYTOX, SYTO BC, DAPI, Hoechst 33342, Hoechst 33258, and PicoGreen. SYBR Green®, which is excited at 497 nm and emits at 520 nm, is preferably used.

Thus, in a particular embodiment the detection of the product of amplification is carried out by means of a fluorescent intercalating agent, wherein said intercalating agent is SYBR Green in an even more particular embodiment.

In addition, the specific detection mechanisms are capable of distinguishing between the sequence of interest and the non-specific amplifications. All of them are based on the use of quenchers (quencher pigment or non-fluorescent quencher -NFQ- which increases the efficacy of the detection and signal since it does not emit fluorescence) and probes labeled with a wide range of fluorophores (reporter pigment) with different excitation and emission spectra.

In the present invention, "fluorophore" is understood as a molecule capable of emitting electromagnetic radiation in response to the absorption of excitation radiation in which the wavelength of the radiation emitted is different from the wavelength of the excitation radiation and wherein the radiation emission lasts only while the excitation radiation is maintained. Illustrative, non-limiting examples of fluorescent markers which can be used in the context of the present invention include:

TABLE 1

The most common fluorescent colorants used

| Molecule | Excitation (nm) | Emission (nm) |
| --- | --- | --- |
| FAM | 488 | 518 |
| HEX | 488 | 556 |
| TET | 488 | 538 |
| CY3 | 550 | 570 |
| CY5.5 | 675 | 694 |
| JOE | 527 | 548 |
| 6-ROX | 575 | 602 |
| Cascade Blue | 400 | 425 |
| Fluorescein | 494 | 518 |
| Texas Red | 595 | 615 |
| Rhodamine | 550 | 575 |
| Rhodamine Green | 502 | 527 |
| Rhodamine Red | 570 | 590 |
| Rhodamine 6G | 525 | 555 |
| 6-TAMRA | 555 | 580 |
| 5-TMRIA | 543 | 567 |
| Alexa 430 | 430 | 545 |
| Alexa 488 | 493 | 516 |
| Alexa 594 | 588 | 612 |
| Bodipy R6G | 528 | 550 |

In the present invention, "quencher" is understood as the molecule which accepts energy from a fluorophore and which dissipates it in the form of heat or fluorescence. Examples of quenchers include but are not limited to Methyl Red, Elle-Quencher, Dabcyl, Dabsyl, TAMRA, etc.

Thus, in a particular embodiment, the detection of the product of amplification is carried out by means of a labeled probe which, in an even more particular embodiment, comprises a reporter pigment at its 5' end and a quencher pigment at its 3' end. Examples of probes having this type of labeling are, for example, TaqMan probes, Molecular Beacons, Scorpion probes, Amplifluor probes, Eclipse probes, etc.

Additionally, if desired, the probe can comprise at its 3' end an MGB molecule between the nucleotide sequence and the quencher pigment. An MGB (minor groove binder) is a small, half moon-shaped molecule which fits very well in the minor groove of double-stranded DNA. Thus, when the probe hybridizes with the target sequence, MGB stabilizes the pairing by being incorporated in the minor groove of the double-stranded DNA created between the probe and said target sequence. The stabilization is much more efficient when the sequences match perfectly (i.e., there is no mismatching). In addition to the superior discriminating potential, the greater stability allows the probes to be shorter (normally 13 to 20 bases) in comparison with standard probes (18 to 40 bases), without jeopardizing the guidelines in the design of the primers. The example illustrating the present invention, in section B, points 1 and 2 (development of the INVAVITONE and INVAVITWO probes respectively) shows the used of said MGB molecules.

In a particular embodiment, the product of amplification is detected by means of a probe comprising the nucleotide sequence shown in SEQ ID NO: 4 [INVAVITWO], which will specifically detect the target region used in the method for detection of *Salmonella* spp. of the present invention, i.e., the region of the *Salmonella* spp. invA gene comprising the region of said gene corresponding to the region comprised between nucleotides 1001 and 1069 in the nucleotide sequence shown in SEQ ID NO: 1.

In the present invention, "the region of *Salmonella* spp. invA gene comprising the region of said gene corresponding to the region comprised between nucleotides 1001 and 1069 in the nucleotide sequence shown in SEQ ID NO: 1" is understood as the region or sequence of the invA gene of any species or variant of *Salmonella* spp. which is homologous to the region comprised between nucleotides 1001 and 1069 of the nucleotide sequence shown in SEQ ID NO: 1.

In the present invention, "homologous sequences" is understood as those sequences having a sequence identity with respect to one another of at least 50%, at least 60%, at least 70%, at least 80%, at least 90%, at least 91%, at least 92%, at least 93%, at least 94%, at least 95%, at least 96%, at least 97%, at least 98% or at least 99%. The expression "sequence identity" relates to the degree in which two polynucleotide sequences in a nucleotide to nucleotide base throughout a particular region of comparison are identical. The percentage of sequence identity can be calculated, for example, by optimally comparing two aligned sequences throughout a region of comparison, determining the number of positions in which identical nucleic acid bases (A, T, C, G, U or I, for example) are located in both sequences to give the number of matching positions, dividing the number of matching positions by the total number of positions in the region of comparison (i.e., the size of the window) and multiplying the result by 100.

The homology between several nucleotide sequences can be determined by conventional methods, for example, by means of standard algorithms of multiple sequence alignment known in the state of the art, such as ClustalW (Chenna, et al. 2003 Nucleic Acids Res, 31:3497-3500), for example. FIG. 2 attached to the present description shows a multiple sequence alignment in which the sequences of the invA gene of different species of *Salmonella* spp. which are homologous to one another are aligned.

Additionally, a particular embodiment of the invention is the inclusion of an internal amplification control in the methods for detection of *Salmonella* sp described in the present description. Thus, it is possible to carry out an amplification reaction in the presence of an exogenous DNA which serves as an internal amplification control, such that it is assured that a negative result in the detection of the microorganism (in the present invention *Salmonella* spp.) is not due to the inhibition of the Taq polymerase by the presence of inhibiting substances, but rather to the lack of complementarity between the probe and the products of amplification or to the absence of amplification by the absence of annealing of the primers. The inclusion of the internal amplification control will allow easily identifying false negative results. Patent application WO2007/085675 and the publication by Alvarez, J. et al. 2004 (J. Clin. Microbiol., 42:1734-1738) describe the preparation of an internal amplification control.

Therefore, in a particular embodiment, the amplification is carried out in the presence of an exogenous DNA whose ends contain sequences that can be amplified using the same primers as those used for amplifying a region of the *Salmonella* spp. invA gene comprising the region of said gene corresponding to the region comprised between nucleotides 1001 and 1069 in the nucleotide sequence shown in SEQ ID NO: 1.

In another even more particular embodiment, the exogenous DNA comprises a fragment of the λ phage genome.

The pair of primers formed by the SEQ ID NO: 5 and SEQ ID NO: 6 sequences [INVAVITONE F/R] are among the pairs of primers identified by the inventors allowing the specific detection of microorganisms of the *Salmonella* spp. genus and even at the variant level.

Thus, in another aspect the invention relates to an in vitro method for the detection of *Salmonella* spp. in a sample (method 2 of the invention) comprising
(i) performing an amplification reaction from a nucleic acid preparation derived from said sample using a pair of primers comprising the SEQ ID NO: 5 and SEQ ID NO: 6 sequences [INVAVITONE F/R]; and
(ii) detecting the product of amplification by means of using a labeled probe, wherein said probe comprises a reporter pigment at its 5' end and a quencher pigment at its 3' end and has the nucleotide sequence shown in SEQ ID NO: 7 [INVAVITONE].

As has been indicated in previous paragraphs, in the present invention "nucleic acid preparation" is understood as the set of nucleic acids, i.e., DNA, RNA and/or cDNA, present in a sample.

The different techniques for extracting nucleic acids, for detecting products of amplification, labeling of probes, etc., previously described for method 1 of the invention can be applied to the present method 2 of the invention.

As in method 1 of the invention, the amplification reaction can be performed in the presence of an exogenous DNA which serves as an internal amplification control. Therefore, in a particular embodiment, the amplification is carried out in the presence of an exogenous DNA whose ends contain sequences that can be amplified using the pair of primers comprising the SEQ ID NO: 5 and SEQ ID NO: 6 sequences [INVAVITONE F/R].

In another even more particular embodiment, the exogenous DNA comprises a fragment of the λ phage genome.

As understood by the person skilled in the art, *Salmonella* spp. is a widely distributed microorganism which can survive in many different environments. Thus, any type of sample suspected of contamination by *Salmonella* spp. can be used in putting the methods for the detection of *Salmonella* spp. described in the present invention into practice. Typically, the sample is a bacterial population associated with an industrial process for producing consumer goods such as, for example, paper industries, refrigeration industries, petroleum industries, oil industries, brewery industries and industries for treatment of waster water or associated with a process for handling biological fluids in the health field such as an enteric perfusion system, dialysis systems, catheter systems and the like. Alternatively, the sample can be of biological origin and comprise tissues, cells, cell extracts, cell homogenates, protein fractions, biological fluids (blood, serum, plasma, urine, synovial fluid, cerebrospinal fluid, feces, sweat, etc.). Alternatively, the sample can consist of entire organs such as muscle, eye, skin, gonads, lymph nodes, heart, brain, lung, liver, kidney, spleen, tumors.

Therefore, in a particular embodiment of the invention, the sample is selected from the group comprising an environmental sample (such as a water or ground sample, for example), a clinical sample (biological fluid, feces, etc.) and a food sample (perishable food products, chicken meat, eggs, creams, etc). Preferably, the sample to be analyzed will be a food sample.

As has been previously indicated, the inventors have developed a set of primers and probes which allow the specific detection of *Salmonella* spp.

Therefore, in another aspect the invention relates to an oligonucleotide the sequence of which is selected from the group of the SEQ ID NO: 2 [INVAVITWO F primer], SEQ ID NO: 3 [INVAVITWO R primer], SEQ ID NO: 4 [INVAVITWO probe], SEQ ID NO: 7 [INVAVITONE probe] sequences.

The kits comprising the reagents and agents necessary for putting the described methods of the present invention into practice form additional aspects thereof.

Thus, in another aspect the invention relates to a kit (kit 1 of the invention) comprising a pair of primers capable of amplifying a region of the *Salmonella* spp. invA gene comprising the region of said gene corresponding to the region comprised between nucleotides 1001 and 1069 in the nucleotide sequence shown in SEQ ID NO: 1.

In a particular embodiment of the kit, the pair of primers comprises the SEQ ID NO: 2 and 3 sequences [INVAVITWO F/R].

In another particular embodiment, said kit furthermore comprises a labeled probe capable of detecting the product of amplification.

In another particular embodiment, the probe comprises a reporter pigment at its 5' end and a quencher pigment at its 3' end.

In a particular embodiment, the probe comprises the nucleotide sequence shown in SEQ ID NO: 4 [INVAVITWO].

In another particular embodiment, the kit furthermore comprises a fluorescent intercalating agent, which in an even more particular embodiment, is SYBR Green.

In another particular embodiment, the kit of the invention furthermore comprises an exogenous DNA whose ends contain sequences that can be amplified using the same primers as those used for amplifying a region of the *Salmonella* spp. invA gene comprising the region of said gene corresponding to the region comprised between nucleotides 1001 and 1069 in the nucleotide sequence shown in SEQ ID NO: 1.

In another even more particular embodiment of said kit, the exogenous DNA comprises a fragment of the λ phage genome.

In another aspect the invention relates to a kit (kit 2 of the invention) comprising (i) the pair of SEQ ID NO: 5/SEQ ID NO: 6 primers [INVAVITONE F/R] and (ii) a labeled probe, wherein said probe comprises a reporter pigment at its 5' end and a quencher pigment at its 3' end and has the nucleotide sequence shown in SEQ ID NO: 7 [INVAVITONE].

In a particular embodiment, said kit furthermore comprises an exogenous DNA whose ends contain sequences that can be amplified using the pair of SEQ ID NO: 5/SEQ ID NO: 6 primers [INVAVITONE F/R], wherein said exogenous DNA comprises a fragment of the λ phage genome in an even more particular embodiment.

Finally, the use of kits 1 and 2 of the invention form additional aspects thereof.

Thus, in one aspect the invention relates to the use of a kit according to what has been described in the present invention for the detection of *Salmonella* spp. in a sample.

In a particular embodiment, the sample is selected from the group comprising an environmental sample, a clinical sample and a food sample.

The following example is illustrative of the invention and it is not intended to be limiting thereof.

Example

Detection of DNA and RNA of *Salmonella* spp. in Food
A. Protocol for the Detection of DNA of *Salmonella* spp.
1. Extraction with CHELEX® 100-6%

CHELEX 100-6% resin was prepared by means of resuspending 1.5 grams of Chelex 100 in 25 ml of bidistilled water and maintaining under moderated stirring. The Chelex 100-6% solution was preserved at 4° C.

For extracting the DNA from *Salmonella* spp., the samples were centrifuged with 1 ml of pre-enriched culture in a 1.5 ml Eppendorf tubes for 5 minutes at 13,000 rpm. The supernatant was removed with a pipette and the pellet was resuspended in 300 µl of CHELEX 100-6, using a vortex. The samples were incubated at 56° C. for 15-20 minutes and stirred using a vortex for 10 seconds. The samples were incubated in a bath at 100° C. for 5 minutes, mixed using a vortex for 10 seconds and the tubes were immediately transferred to ice. The samples were centrifuged for 5 minutes at 13,000 rpm. 200 µl of supernatant (containing DNA) were transferred to another tube in which it was preserved at 4° C. if it was going to be used in a few days or at −20° C. for its longer-term preservation.
2. Creation of the Internal Real Time PCR Amplification Control with SYBR Green InvA ICF (SEQ ID NO: 8) and invA ICR (SEQ ID NO: 9) primers with the following sequence were used to obtain an internal control:

```
invA ICF (SEQ ID NO: 8):
5'-GTGAAATTATCGCCACGTTCGGGCAAGCAGAACGAAAAAGGT
GAGC-3' invA ICR (SEQ ID NO: 9):
5'-TCATCGCACCGTCAAAGGAACCCTGCACTGCTCAATGCGCCA-3'
```

The underlined sequences belong to primers 139 and 141 which amplify the invA gene of *Salmonella* (Malorny et al., 2003, Appl. Environ. Microbiol. 69:290-296), whereas the sequences in bold print belong to λ phage, which are incorporated to form part of the primers and to be able to amplify a fragment of the λ phage to convert it into an internal control. These primers are used to amplify a 348 by fragment of λ phage (SEQ ID NO: 10):

```
5'-gtgaaattatcgccacgttcgggcaaGCAGAACGAAAAAGGTGAGC

CGGTCACCTGGCAGGGGCGACAGTATCAGCCGTATCCCATTCAGGGGAG

CGGTTTTGAACTGAATGGCAAAGGCACCAGTACGCGCCCCACGCTGACG
```

-continued

```
GTTTCTAACCTGTACGGTATGGTCACCGGGATGGCGGAAGATATGCAGA

GTCTGGTCGGCGGAACGGTGGTCCGGCGTAAGGTTTACGCCCGTTTTCT

GGATGCGGTGAACTTCGTCAACGGAAACAGTTACGCCGATCCGGAGCAG

GAGGTGATCAGCCGCTGGCGCATTGAGCAGTGCAGggttcctttgacgg tgcgatga-3'
```

This fragment corresponds to the internal control, which in real time PCR with SYBR-GREEN allows amplifying a fragment of the lambda phage with the same primers which are used to detect *Salmonella* (primers 139 and 141).

To obtain the internal control a conventional PCR was performed using as a template a preparation of λ phage digested with EcoRI and HindIII (SIGMA) using the following reaction mixture:

| | Concentration [initial] | Concentration [final] | x1 |
|---|---|---|---|
| PCR Buffer | 10X | 1X | 2.5 µl |
| MgCl2 | 50 mM | 1.5 mM | 0.75 µl |
| dNTP Mix | 25 mM | 0.25 mM | 0.25 µl |
| invA ICF | 10 µM | 0.4 µM | 1 µl |
| invA ICR | 10 µM | 0.4 µM | 1 µl |
| Taq Polymerase | 5 U | 1 U | 0.2 µl |
| DNA (λ phage) | | | 1 µl |
| Water | | | 18.30 µl |
| Final volume | | | 25 µl | and the following PCR conditions:

| 1 cycle | 95° C. | 1 minute |
|---|---|---|
| 35 cycles | 95° C. | 30 seconds |
| | 60° C. | 30 seconds |
| | 72° C. | 30 seconds |
| 1 cycle | 72° C. | 10 minutes |

Once PCR was performed, it was verified that amplification of the products occurred. For that purpose electrophoresis was performed in 2% agarose gel. Part of the samples was loaded in the wells of the gel, for example: 5 µl sample+5 µl of loading buffer. The gel was stained with ethidium bromide and it was verified that the band with the desired size appears.

A purification of the DNA obtained in PCR was subsequently performed using the rest of the sample which had not been loaded in the gel. The purification was done with the kit specific for it, such as the QIAquick PCR Purification Kit (QIAGEN), following the protocol established by the company.

The obtained product was the internal control, which was stored at −20° C. as a stock. Starting from the stock a $10^{-5}$ dilution was used in the real time PCR with SYBR-GREEN.
3. Detection of *Salmonella* spp. with SYBR-Green PREMIX EX TAQ® (TAKARA)

The detection of *Salmonella* by means of real time PCR using SYBR-Green was carried out using the reaction mixture:

| MASTER SYBR-GREEN | 10 µl |
|---|---|
| Primer F (139) | 1 µl |

| -continued | | |
|---|---|---|
| Primer R (141) | 1 µl | |
| ROX | 0.4 µl | |
| Internal Control (R2 dil −5) | 1 µl | |
| DNA | 3 µl | |
| Water | 3.6 µl | |
| Final volume= | 20 µl | | and the following amplification conditions:

| 1 CYCLE | 95° C. | 1 minute |
|---|---|---|
| 40 CYCLES | 95° C. | 15 seconds |
| | 60° C. | 1 minute |

4. Detection of the *Salmonella* spp. invA Gene by Means of Real Time PCR Amplification and SYBR-Green During the first part of the invention a genomic study of the *Salmonella* spp. genus was carried out for the selection of targets suitable for detection of this pathogen in food samples. The chosen genomic target was the invA gene, already proposed by several authors (Malorny et al., above). This gene plays an important role in the mechanisms of invasion and survival of *Salmonella* spp., therefore the sequence of said gene had to be transcribed in the messenger RNA in most of the serotypes of the genus. The methodology of conventional PCR (already published, primers 139 and 141) (Malorny et al., se above) was fine-tuned below based on the *Salmonella* spp. invA gene. Likewise, the methodology for DNA extraction based on commercial CHELEX 100 silica resin was fine-tuned (see section 1).

The amplification was performed using real time PCR ABI PRISM® 7000 Sequence Detection System equipment (Applied Biosystems). This technique allowed the specific and fast detection of DNA of *Salmonella* spp. (see Table 1).

TABLE 1

Detection of DNA in *Salmonella* spp. serotypes by means of real time PCR using SYBR-Green and primers 139 and 141.

| Strain number | Microorganism | SYBR (Takara) |
|---|---|---|
| 75 UPV/EHU | *S. typhimurium* DT169 | + |
| 26 UPV/EHU | *S. enteritidis* PT4 | + |
| 340 UPV/EHU | *S. california* | + |
| 4 UPV/EHU | *S. arizonae* | + |
| 456 UPV/EHU | *S. hadar* | + |
| 240 UPV/EHU | *Salmonella* IV 48 | + |
| 328 UPV/EHU | *S. montevideo* | + |
| 291 UPV/EHU | *Salmonella* 4.5, 12:i:- | + |
| 128 UPV/EHU | *S. typhimurium* DT104 | + |
| 39 UPV/EHU | *S. enteritidis* PT4 | + |
| 7 UPV/EHU | *S. virchow* | + |
| 8 UPV/EHU | *S. miami* | + |
| 10 UPV/EHU | *S. abony* | + |
| 59 UPV/EHU | *S. dublin* | + |
| 247 UPV/EHU | *S. blockley* | + |
| 312 UPV/EHU | *S. heidelberg* | + |
| 271 UPV/EHU | *S. anatum* | + |
| 270 UPV/EHU | *S. muenchen* | + |
| 273 UPV/EHU | *S. litchfield* | + |
| 276 UPV/EHU | *S. fayed* | + |
| 275 UPV/EHU | *S. hadar* | + |
| 119 UPV/EHU | *S. enteritidis* PT1 | + |
| 235 UPV/EHU | *S. lindenburg* | + |
| 232 UPV/EHU | *S. cremieu* | + |
| 246 UPV/EHU | *S. duesseldorf* | + |
| 238 UPV/EHU | *S. cubana* | + |
| 241 UPV/EHU | *S. braenderup* | + |

TABLE 1-continued

Detection of DNA in *Salmonella* spp. serotypes by means of real time PCR using SYBR-Green and primers 139 and 141.

| Strain number | Microorganism | SYBR (Takara) |
|---|---|---|
| 259 UPV/EHU | S. IV 6, 14 | + |
| 257 UPV/EHU | S. IIIb 58 | + |
| 264 UPV/EHU | S. IIIa 48 | + |
| 261 UPV/EHU | *S. miami* | + |
| 268 UPV/EHU | *S. hadar* | + |
| 263 UPV/EHU | *S. agona* | + |
| 169 UPV/EHU | *S. enteritidis* PT4 | + |
| 175 UPV/EHU | *S. enteritidis* PT1 | + |
| 183 UPV/EHU | *S. enteritidis* PT1 | + |
| 192 UPV/EHU | *S. enteritidis* PT8 | + |
| 202 UPV/EHU | *S. enteritidis* PT2 | + |
| 205 UPV/EHU | *S. enteritidis* PT8 | + |
| 69 UPV/EHU | *S. typhimurium* 59 | + |
| 72 UPV/EHU | *S. typhimurium* DT66 | + |
| 74 UPV/EHU | *S. typhimurium* DT12 | + |
| 76 UPV/EHU | *S. typhimurium* DT120 | + |
| 78 UPV/EHU | *S. typhimurium* DT193 | + |
| 245 UPV/EHU | *S. typhimurium* DT52 | + |
| 20 UPV/EHU | *S. arizonae* | + |
| 250 UPV/EHU | S. IIIb 48 | + |
| 314 UPV/EHU | S. IIIa 48 | + |
| UPV/EHU | *P. vulgaris* (CECT* 484) | − |
| UPV/EHU | *E. cloacae* (CECT 679) | − |
| UPV/EHU | *C. freundii* | − |
| UPV/EHU | *K. pneumoniae* | − |
| UPV/EHU | *P. aeruginosa* | − |
| UPV/EHU | *E. coli* (CECT 679) | − |
| UPV/EHU | *H. alvei* (CECT 158T) | − |
| UPV/EHU | *Shigella* sp, (CECT 583) | − |

*CECT = Spanish Type Culture Collection

B. Protocol for the Detection of *Salmonella* spp. RNA

1. Development of the INVAVITONE Probe

In the second part of the invention, the methodology developed for DNA was extrapolated for the detection of messenger RNA so that the assay will allow distinguishing between the detection of live and dead *Salmonella* cells and therefore give an added value to the detection system developed in the present invention. To that end, primers and a probe were designed taking into account their inclusion in the invA gene. In the design of the probes and the primers flanking it, the genetic bases which include known information about *Salmonella* spp. were analyzed and thus specific sequences that were present in all the *Salmonella* spp. serotypes were generated. Finally and by means of the Primer Express® program a probe which was referred to as INVAVITONE was designed.

| INVAVITONE-F | SEQ ID NO: 5 | 5'-TTAAATTCCGTGAAGCAAAAC GTA-3' |
|---|---|---|
| INVAVITONE-R | SEQ ID NO: 6 | 5'-AACCAGCAAAGGCGAGCA-3' |
| INVAVITONE probe | SEQ ID NO: 7 | 5'-CGCAGGCACGCC-3' |

The assay for the detection of *Salmonella* spp. by means of using TaqMan-MGB® probe (INVAVITONE) and the primers flanking it (INVAVITONE-F and INVAVITONE-R) was performed using the real time PCR ABI PRISM® 7000 Sequence Detection System equipment (Applied Biosystems). TaqMan-MGB® probe, synthesized by Applied Biosystems, has VIC fluorophore at its 5' end acting as a "reporter" and a non-fluorescent quencher (NFQ) at its 3' end and an MGB (minor groove binder) terminal tail.

Different *Salmonella* spp. serotypes, in addition to another series of related microorganisms which were used as negative detection controls, were analyzed. The inclusion of these negative controls also served to verify the specificity of the probe. All the isolations were analyzed on repeated occasions to verify the reproducibility of the technique. These microorganisms and their Ct (Cycle threshold) values are indicated in Table 2. This Ct value is the cycle in which the sample crosses or exceeds a fluorescence level which separates the background fluorescence from the fluorescence itself of the amplification. When working with actual DNA extractions in which the amount of starting molecules is unknown, the Ct value varies depending on this amount (FIG. 1). The results of the detection are shown in Table 2.

As is observed in Table 2, the designed probe was capable of detecting the most common *Salmonella* spp. serotypes in our environment. Nevertheless, some assays with foreign serotypes not common in the area did not give the expected positive result. For the purpose of assuring an optimal result in the detection of *Salmonella* spp., the design of a new probe with the same features as that tested one, but with the capacity to detect a larger number of serotypes, was proposed.

The INVAVITONE probe was also used to detect *Salmonella* spp. in real food samples from Laboratorios Bromatológicos Araba. The samples were obtained from several real food matrices. The DNA was extracted by means of the extraction protocol with Chelex and the hybridization was performed in the thermocycler. The detection was analyzed in

TABLE 2

Detection of DNA in *Salmonella* spp. serotypes by means of real time PCR using INVAVITONE probe.

| Microorganism | | Ct | Microorganism | | Ct |
|---|---|---|---|---|---|
| *S. enteritidis* 26 UPV/EHU | + | 15.81 | *S. enteritidis* 169 UPV/EHU/PT4 | + | 15.81 |
| *S. typhimurium* 75 UPV/EHU | + | 13.33 | *S. enteritidis* 175 UPV/EHU/PT1 | + | 19.34 |
| *S. california* 340 UPV/EHU | + | 15.61 | *S. enteritidis* 183 UPV/EHU/PT1 | + | 12.81 |
| *S. hadar* 456 UPV/EHU | + | 19.00 | *S. enteritidis* 192 UPV/EHU/PT8 | + | 13.22 |
| *Salmonella* IV 48 240 UPV/EHU | − | Undet. | *S. enteritidis* 202 UPV/EHU/PT2 | + | 12.39 |
| *S. montevideo* 328 UPV/EHU | + | 19.77 | *S. enteritidis* 205 UPV/EHU/PT8 | + | 13.95 |
| S. 4,5, 12:i:- 291 UPV/EHU | + | 14.01 | *S. typhimurium* 59 UPV/EHU | + | 13.00 |
| *S. typhimurium* DT 104 128 UPV/EHU | + | 14.25 | *S. typhimurium* 72 UPV/EHU | + | 13.20 |
| *S. enteritidis* PT4 39 UPV/EHU | + | 16.13 | *S. typhimurium* 74 UPV/EHU | + | 13.75 |
| *S. virchow* 7 UPV/EHU | + | 17.80 | *S. typhimurium* 76 UPV/EHU/DT120 | + | 12.75 |
| *S. miami* 8 UPV/EHU | + | 19.21. | *S. typhimurium* 78 UPV/EHU | + | 18.22 |
| *S. abony* 10 UPV/EHU | + | 16.30 | *S. typhimurium* 245 UPV/EHU | + | 11.77 |
| *S. dublin* 59 UPV/EHU | + | 13.28 | *S. arizonae* 20 UPV/EHU | − | Indet |
| *S. block* 247 UPV/EHU | + | 13.24 | *Salmonella* IIIb 48 250 UPV/EHU | − | Indet |
| *S. heidelberg* 312 UPV/EHU | + | 19.65 | *Salmonella* IIIa 48 314 UPV/EHU | − | Indet |
| *S. anatum* 271 UPV/EHU | + | 21.98 | *Salmonella* IIIb 58 257 UPV/EHU | − | Indet |
| *S. muenchen* 270 UPV/EHU | + | 18.04 | *Salmonella* IIIa 48 264 UPV/EHU | − | Indet |
| *S. linch* 273 UPV/EHU | + | 15.82 | *S. miami* 261 UPV/EHU | + | 19.88 |
| *S. fayed* 276 UPV/EHU | + | 19.64 | *S. hadar* 268 UPV/EHU | + | 16.13 |
| *S. hadar* 275 UPV/EHU | + | 19.38 | *S. agona* 263 UPV/EHU | + | 9.24 |
| *S. enteritidis* 119 UPV/EHU | + | 11.12 | *P. vulgaris* UPV/EHU | − | Indet |
| *S. linder* 235 UPV/EHU | + | 12.08 | *E. cloacae* UPV/EHU | − | Indet |
| *S. cremieu* 232 UPV/EHU | + | 15.19 | *C. freundii* UPV/EHU | − | Indet |
| *S. duess* 246 UPV/EHU | + | 13.40 | *K. pneumoniae* UPV/EHU | − | Indet |
| *S. cubana* 238 UPV/EHU | + | 9.56 | *P. aeruginosa* UPV/EHU | − | Indet |
| *S. braenderup* 241 UPV/EHU | + | 17.41 | *E. coli* CECT 679 UPV/EHU | − | Indet |
| *Salmonella* IV 6, 14 259 UPV/EHU | + | 19.24 | *H. alvei* UPV/EHU | − | Indet |
| | | | *Shigella* sp, UPV/EHU | − | Indet | parallel by means of immunoconcentration with the MiniVidas® equipment of the Biomerieux company. The number of samples analyzed was 170, including on some occasions replicas from the same food or colonies belonging to the same samples.

Likewise, the INVAVITONE probe was used to verify the detection of messenger RNA in food matrices inoculated with *Salmonella* spp. serotypes. After their incubation in enrichment broths for 24 hours at 37° C., the RNA was extracted by means of a commercial kit (Nalgery-Machinery®). The application of the reverse transcription of the RNA derived from the different cDNA extraction tests, by means of using the Applied-Biosystems commercial kit, allowed the real time detection thereof after amplification and hybridization with the INVAVITONE probe in the ABI-PRISM 7000 SDS® thermocycler (Applied Biosystems).

During this phase of the invention the improvement of the specific probe of *Salmonella* spp. INVAVITONE, internal amplification controls as well as development of another probe with the capacity to detect the internal control were approached for the purpose of obtaining the reagents necessary and sufficient for the development of a commercial kit for detecting this pathogen. By taking the invA gene sequence as a basis, primers flanking the region corresponding to the amplification and hybridization of the INVAVITONE probe, which would generate a fragment of approximately 300 base pairs which could be sequenced by automatic processes, were designed. Once the primers were synthesized by the company Qiagen-Izasa, they were used to amplify the mentioned sequence in the *Salmonella* spp. serotypes by PCR with negative hybridization with the INVAVITONE probe, together with positive controls. DNA bands were obtained with the expected sizes which, after their purification by means of the commercial kit, were sent for their sequencing to the company, Sistemas Genómicos. The obtained gene sequences were analyzed by means of the ClustalW alignment program for the purpose of determining the reasons causing the lack of amplification and hybridization with the INVAVITONE probe. Genetic polymorphisms were found at nucleotide level which clearly justified the absence of reactivity. In other words, although the gene is present in most of the serotypes, its detection is not possible due to silent mutations that may invalidate this sequence for its diagnosis use due to its lack of hybridization with the probe. An added problem is the existence of several thousand different serotypes of this microorganism, of which only a few are completely sequenced and their sequences deposited in International databases at the disposal of the scientific community.

2. Development of the INVAVITWO Probe

Starting from the information obtained by means of sequencing the serotypes that did not react with the INVAVITONE probe plus the information available at that time in the genetic bases, a new version of the *Salmonella* spp. specific probe was developed, seeking a more stable site with lower alteration at the nucleotide level within the invA gene.

For the development of the second probe, real time PCR equipment referred to as iQcycler® was acquired from the company Bio-Regulatory Affairs Documentation, which did not have the filter necessary for reading with the VIC fluorophore (used in the INVAVITONE probe), which determined the selection of fluorophores for the labeling of the second probe. The latter was designed by means of the Primer Express® program and the company Applied Biosystems was asked for its labeling at 5' with 6-FAM fluorophore, compatible for its detection in both pieces of real time PCR equipment.

The second probe developed by this equipment was referred to as INVAVITWO. The sequence of the new primers and of the new TaqMan-MGB® probe is the following:

| INVAVITWO-F | SEQ ID NO: 2 | 5'-AAAGGAAGGGACGTCGTT AGG-3' |
|---|---|---|
| INVAVITWO-R | SEQ ID NO: 3 | 5'-CAGTGGTACGGTCTCTGT AGAAACTT-3' |
| INVAVITWO probe | SEQ ID NO: 4 | 5'-FAM-CTGATTGGCGATCT C-MGB-3' |

Likewise, the concentrations of new TagMan-MGB® probe, as well as the concentration of the two primers, were optimized. The optimal concentrations of the primers and of the TaqMan-MGB® probe by reaction are indicated in Table 3.

TABLE 3

Optimal concentrations of the primers and of the INVAVITWO probe.

| PRIMERS[1] AND PROBES[2] | CONCENTRATION |
|---|---|
| INVAVITWO-F[1] | 400 nM |
| INVAVITWO-R[1] | 400 nM |
| INVAVITWO[2] | 100 nM |

The amplification reactions were carried out using the following reaction mixture

| MASTER | 12.5 µl |
|---|---|
| INVAVITWO-F primer | 1 µl |
| INVAVITWO-R primer | 1 µl |
| INVAVITWO probe | 0.25 µl |
| Internal control (dil. $10^{-4}$) | 3 µl |
| CI probe | 0.25 µl |
| DNA | 5 µl |
| Water | 2 µl |
| Final Volume= | 25 µl | and the following amplification conditions:

| 1 CYCLE | 50° C. | 2 minutes |
|---|---|---|
| 1 CYCLE | 95° C. | 10 minutes |
| 36 CYCLES | 95° C. | 15 minutes |
|  | 60° C. | 1 minute |

An amplification master having AmpErase® uracil-N-glycosylase (UNG) was chosen. UNG is a 26-kDa recombinant enzyme which allows eliminating the contamination with amplified products derived from previous amplification cycles: the enzyme degrades the DNA incorporating dUTPs instead of the dTTPs of the "natural DNA". This will hinder the onset of false positives by the mentioned contamination.

The INVAVITWO probe was evaluated in relation to the test of inclusivity and exclusivity with a wide collection of DNAs derived from the collection of *Salmonella* spp. serotypes available in the Facultad de Farmacia (School of Pharmacy) of the UPV/EHU, together with strains of other microorganisms belonging to other species. As can be seen in the attached table (Table 4), the results remarkably improved with respect to the INVAVITONE probe, since it detected virtually all the tested serotypes (inclusivity), together with a great exclusivity since no false positive had been detected in other studied microorganisms (Table 4).

TABLE 4

Results of the detection of *Salmonella* spp. serotypes by means of the INVAVITWO probe.

| Microorganism | | Ct | Microorganism | | Ct |
|---|---|---|---|---|---|
| S. enteritidis 26 UPV/EHU | + | 27.16 | S. enteritidis PT4 169 UPV/EHU | + | 27.89 |
| S. typhimurium 75 UPV/EHU | + | 17.9 | S. enteritidis PT1 175 UPV/EHU | + | 29.46 |
| S. california 340 UPV/EHU | + | 28.21 | S. enteritidis PT1 183 UPV/EHU | + | 29.22 |
| S. hadar 456 UPV/EHU | + | 28.6 | S. enteritidis PT8 192 UPV/EHU | + | 27.9 |
| S. IV 48 240 UPV/EHU | + | 14.23 | S. enteritidis PT2 202 UPV/EHU | + | 27.36 |
| S. montevideo 328 UPV/EHU | − | Undet | S. Enteritidis PT8 205 UPV/EHU | + | 31.47 |
| S. 4:5:12:I:- 10B- UPV/EHU | + | 17.43 | S. typhimurium 59 UPV/EHU | + | 18.06 |
| S. typhimurium DT104 128 UPV/EHU | + | 19.02 | S. typhimurium DT66 72 UPV/EHU | + | 18.45 |
| S. enteritidis PT4 39 UPV/EHU | + | 28.08 | S. typhimurium DT12 74 UPV/EHU | + | 17.46 |
| S. virchow 7 UPV/EHU | + | 17.37 | S. typhimurium DT120 76 UPV/EHU | + | 18.19 |
| S. miami 8 UPV/EHU | + | 26.31 | S. typhimurium DT193 78 UPV/EHU | + | 18.15 |
| S. abony 10 UPV/EHU | + | 18.37 | S. typhimurium DT52 245 UPV/EHU | + | 17.65 |
| S. dublin 59 UPV/EHU | + | 30.5 | S. arizonae 20 UPV/EHU | + | 12.61 |
| S. blockley 247 UPV/EHU | + | 18.36 | S. IIIb 48 250 UPV/EHU | + | 12.87 |
| S. heidelberg 312 UPV/EHU | + | 18.72 | S. IIIa 48 314 UPV/EHU | + | 14.34 |
| S. anatum 271 UPV/EHU | + | 18.79 | S. IIIb 58 257 UPV/EHU | + | 16.26 |
| S. muenchen 270 UPV/EHU | + | 22.23 | S. IIIa 48 264 UPV/EHU | + | 15.02 |
| S. litchfield 273 UPV/EHU | + | 19.05 | S. miami 261 UPV/EHU | + | 24.5 |
| S. fayed 276 UPV/EHU | + | 32.55 | S. hadar 268 UPV/EHU | + | 17.99 |
| S. hadar 275 UPV/EHU | + | 18.22 | S. agona 263 UPV/EHU | + | 23.42 |
| S. enteritidis PT1 119 UPV/EHU | + | 30.58 | P. vulgaris UPV/EHU | − | Indet |
| S. lindenburg 235 UPV/EHU | + | 16.89 | E. cloacae UPV/EHU | − | Indet |
| S. cremieu 232 UPV/EHU | + | 18.53 | C. freundii UPV/EHU | − | Indet |
| S. duesseldorf 246 UPV/EHU | + | 25.38 | K. pneumoniae UPV/EHU | − | Indet |
| S. cubana 238 UPV/EHU | + | 24.98 | P. aeruginosa UPV/EHU | − | Indet |
| S. Braenderup 241 UPV/EHU | + | 18 | E. coli CECT 679 UPV/EHU | − | Indet |
| S. IV 6, 14 259 UPV/EHU | + | 19.04 | H. alvei UPV/EHU | − | Indet |
| | | | Shigella sp. UPV/EHU | − | Indet |

The INVAVITWO probe was tested with actual samples in Laboratorios Bromatológicos Araba by means of extracting DNA using the Chelex protocol in parallel with the immunoconcentration technique with the MiniVidas equipment of the company Biomerieux, and using the iQcycler equipment of the company Bio-Rad. The number of food samples analyzed with both procedures exceeds 200.

3. Development of the Internal Amplification Control for the INVAVITWO Probe

The study of PCR for the detection of pathogens in food can be affected by the presence of substances present in food matrices with the capacity to inhibit the Taq polymerase enzyme present in the reaction. For this reason a control DNA that can be co-amplify itself, such that it can be assured that a negative result with the specific probe of the microorganism is not due to the inhibition of the Taq polymerase, but rather to a lack of complementarity between the probe and the sequence or due to the absence of amplification by the absence of annealing of the primers.

A strategy for obtaining chimeric DNA generated by amplification of a specific fragment of the λ bacteriophage modified by means of adding ends complementary to the INVAVITWO-F and INVAVITWO-R primers by means of PCR was designed. After its detection by means of electrophoresis and purification by means of commercial kit, the internal control was diluted to 1/10,000 for its incorporation as a positive control DNA in the samples.

A purification of the DNA which had been obtained in PCR was subsequently performed using the rest of the sample which has not been loaded in the gel. The purification was done with a kit specific for it [QIAquick PCR Purification Kit (QIAGEN)], following the manufacturer's instructions.

The obtained product is the internal control, which was stored at −20° C. as a stock.

The amplification of the lambda phage was carried out with the pair of CI INVAVITWO-F (SEQ ID NO: 11) and CI INVAVITWO-R (SEQ ID NO: 12) primers with the sequence:

```
CI INVAVITWO-F (SEQ ID NO: 11):
5'-AAAGGAAGGGACGTCGTTAGGGTGCGGTTATAGCGGTC-3'

CI INVAVITWO-R (SEQ ID NO: 12):
5'-TCAGTGGTACGGTCTCTGTAGAAACTTCGGAACTTACAACC-3'
```

The underlined sequences belong to the INVAVITWO-F and INVAVITWO-R primers which amplify the *Salmonella* invA gene, whereas the sequences in bold print belong to the λ phage which are incorporated to form part of the primers and be able to amplify a fragment of the λ phage, converting it into internal control.

The PCR reaction for generating the internal control is carried out by means of amplification of a DNA sample of the lambda phage digested with EcoRI and HindIII (SIGMA) using the following reaction mixture:

|  | [initial] | [final] | x1 |
|---|---|---|---|
| PCR Buffer | 10X | 1X | 2.5 µl |
| MgCl2 | 50 mM | 1.5 mM | 0.75 µl |
| dNTP Mix | 25 mM | 0.25 mM | 0.25 µl |
| CI INVAVITWO-F | 10 µM | 0.4 µM | 1 µl |
| CI INVAVITWO-R | 10 µM | 0.4 µM | 1 µl |
| Taq Polymerase | 5 U | 1 U | 0.2 µl |
| DNA (λ phage) |  |  | 1 µl |
| Water |  |  | 18.30 µl |
| Final volume |  |  | 25 µl | and the following PCR conditions

| 1 cycle | 95° C. | 1 minute |
|---|---|---|
| 35 cycles | 95° C. | 30 seconds |
|  | 60° C. | 30 seconds |
|  | 72° C. | 30 seconds |
| 1 cycle | 72° C. | 10 minutes |

Once PCR was performed, it was verified that amplification of the products had occurred. For that purpose, electrophoresis was performed in 2% agarose gel. Part of the samples was loaded in wells of the gel (5 µl sample+5 µl of loading buffer) and the gel was stained with ethidium bromide to verify that the band with the desired size appeared. These primers amplify a 150 bp fragment of λ phage (SEQ ID NO: 13):

```
5'AAAGGAAGGGACGTCGTTAGGGTGCGGTTATAGCGGTCCGGCTGTCG

CGGATGAATATGACCAGCCAACGTCCGATATCACGAAGGATAAATGCAG

CAAATGCCTGAGCGGTTGTAAGTTCCGAAGTTTCTACAGAGACCGTACC

ACTGA3'
```

This fragment will be the internal control, which in the real time PCR will amplify with the same primers which are used to detect *Salmonella* (INVAVITWO-F and INVAVITWO-R). The product of amplification of the internal control is detected by means of using a specific probe of sequence TGCGGTTATAGCGGTCCGGCTG (SEQ ID NO: 14) labeled at 5' with TAMRA fluorophore and at 3' with DDQI (Deep Dark Quencher I) such that the probe has the sequence

```
                                    (SEQ ID. NO. 14)
5' TAMRA-TGCGGTTATAGCGGTCCGGCTG-DDQI 3'

(SEQ ID. NO. 13)
5'AAAGAAGGGACGTCGTTAGGGTGCGGTTATAGCGGTCCGGCTGTCGC

GGATGAATATGACCAGCCAACGTCCGATATCACGAAGGATAAATGCAGC

AAATGCCTGAGCGGTTGTAAGTTCCGAAGTTTCTACAGAGACCGTACCA

CTGA3'
``` wherein the area of the internal control in which the probe will hybridize is shown in bold print and underlined.

4. Isolation of the RNA and Reverse Transcription Thereof

After being subjected to treatments of pasteurization, sterilization or radiation, the bacterial DNA can be detected by PCR. This is a proven fact that has been observed upon subjecting different DNA extractions to different treatments of pasteurization and sterilization. This involves being able to detect a dead bacterium (its DNA) and being considered as a positive result, giving rise to a false positive. It then seems clear that the strategy for detecting live cells, or in the phase of replication, can pass through the detection of mRNA.

Once the mRNA is isolated, it is transformed into cDNA by means of the reverse transcriptase in the process referred to as reverse transcription PCR (RT-PCR). Once transformed into cDNA, it was detected by real time PCR by means of the INVAVITWO probe (SEQ ID NO: 4) labeled with fluorescence.

*Salmonella* RNA was then extracted with commercial methods (NucleoSpin® Machery-Nagel for RNA) (see protocol in point 4.1) after which it was treated with DNase to eliminate the possible contaminating DNA which could give rise to a false positive. The RNA was stored at −80° C. for its preservation or at −20° C. if the subsequent analysis will be immediately performed.

The RNA extractions were measured in a NanoDrop® ND-100 spectrophotometer and good measurements were obtained. The obtained ratios 260/280 were 2 or values close to 2. The amount of RNA extracted was low therefore it was not possible to visualize RNA when making denaturizing agarose gels with formaldehyde. However the amount of RNA was enough for being used as a target in a RT-PCR. In RT-PCRs, the efficacy of transfer from RNA to cDNA is not high, but still the subsequent detection with TaqMan-MGB® probes was sensitive enough to solve this drawback. An RT-PCR protocol of the company Applied Biosystems was used with 5 µl of initial RNA sample (see protocol in point 4.1).

The DNA extraction was carried out by means of the NUCLEOSPIN® kit. To that end, samples of 1 ml of culture in a 1.5 ml tube were centrifuged for 5 min at 13000 rpm. The pellet was resuspended in 50 µl of TEL (TE buffer containing 0.2 mg/ml of lysozyme) and incubated for 10 minutes at 37° C. Then 350 µl of RA1 buffer and 3.5 µl of β-mercaptoethanol were added. The content was transferred to the NucleoSpin® Filter units which were centrifuged for 1 minute at 11,000 rpm. 350 µl of ethanol (70%) were added to the filtrate and transferred to the NucleoSpin® RNA II columns, it was centrifuged for a few seconds at 8,000 rpm and the column was transferred to a new collector. Then 350 µl of MDB (Membrane Desalting Buffer) were added, the columns were centrifuged for 1 minute at 11000 rpm.

Then, 95 µl of a standard solution of DNase formed by 10 µl of DNase I and 90 µl of DNase reaction buffer were added to each column. The columns were incubated for 15 minutes at ambient temperature. Then, 200 µl of RA2 buffer were added to each column and they were mixed once in the centrifuge at 8,000 rpm. The columns were transferred to a new collector. Then, 600 µl of RA3 buffer were added, and they were mixed once in the centrifuge at 8,000 rpm, the filered liquid was discarded and the column was placed again in this same collector. Then 250 µl of RA3 buffer were added. The columns were centrifuged for 2 minutes at 11,000 rpm to dry the filter entirely. The column was transferred to a 1.5 ml tube and then 60 µl of (RNase-free) $H_2O$ were added and the columns were centrifuged for 1 minute at 11,000 rpm. The content of the tube was collected.

The reverse transcription reaction was carried out using the following reaction mixture:

| | |
|---|---|
| 10 X TaqMan RT buffer | 1.0 µl |
| 25 mM $MgCl_2$ | 2.2 µl |
| DeoxyNTPs (2.5 mM) | 2.0 µl |
| Random Hexamers (50 µM) | 0.5 µl |
| RNase Inhibitor (20 U/µl) | 0.2 µl |
| MultiScribe Reverse Transcriptase | 0.25 µl |
| RNA sample | 3.85 µl |
| Final volume= | 10 µl | using the following conditions:

| | | |
|---|---|---|
| 1 CYCLE | 25° C. | 10 MINUTES. |
| 1 CYCLE | 48° C. | 30 MINUTES. |
| 1 CYCLE | 95° C. | 5 MINUTES. |

The RNA extractions were stored frozen, although if they were going to be used sooner they were stored at −20° C., and if they were going to be used later at −80° C.

The obtained results were valid, detecting cDNA in all the assays performed and no type of contaminating DNA was detected in the RNA extractions. This meant that the cDNA detected was a copy of the extracted RNA, which in turn is indicative of the bacterial activity. Real time RT-PCR assays have been performed using pure cultures of several different bacterial species of the *Salmonella* genus from the isolation archive of the Departamento de Inmunologia, Microbiologia y Parasitologia (Immunology, Microbiology and Parasitology Department) of the UPV/EHU. In parallel, tests with samples of pure culture of several boiled, sterilized and pasteurized *Salmonella* strains were performed. Samples of *E. coli* strain CECT 679 and *Shigella* sp strain CECT 583 were used as negative controls. The obtained results were very satisfactory, such that the different tested samples of *Salmonella* were detected. The negative controls and the pasteurized and boiled samples also gave the expected result. The specificity and resolution of the TaqMan MGB technology proved to be capable of detecting very low amounts of mRNA, therefore the tested real time RT-PCR technique is valid for the detection of viable *Salmonella* spp. cells.

C. Detection of mRNA of *Salmonella* spp. in Food

The purpose of the assay was to verify the methods for the detection of DNA and messenger RNA, reverse transcription, hybridization with probes in real time and the detection of the internal amplification controls in different food matrices by inoculating all of them artificially with the control strain *Salmonella enterica* serotype *Typhimurium* no. 75 of the culture collection of the UPV/EHU.

The food matrices used in this assay, numbered in the same way, were the following:

1. Chicken autoclaved and subsequently inoculated with the control strain in buffered peptone water, incubated at 37° C., for 24 hours.
2. Fish autoclaved and subsequently inoculated with the control strain in buffered peptone water, incubated at 37° C., for 24 hours.
3. Pastry autoclaved and subsequently inoculated with the control strain in buffered peptone water, incubated at 37° C., for 24 hours.
4. TSB medium inoculated with the control strain, incubated at 37° C., for 24 hours.

Two methods for extracting the genetic material were used:

DNA extraction with the Chelex protocol.

RNA extraction with the NucleoSpin commercial kit.

Once the DNA extractions of each of these samples were obtained, they were stored at 4° C. for their later use. In the case of the RNA, once the extraction protocols were performed, reverse transcription was performed to thus convert the RNA into cDNA. Once the samples of DNA and cDNA are obtained, amplification/detection with the INVAVITWO probe in real time PCR was performed. This probe is labeled with the FAM fluorophore and is responsible for detecting the presence of *Salmonella*. An internal amplification control was also added in each sample, which control is detected by a probe labeled with TAMRA, which serves as an indicator that inhibition has not occurred in the amplification.

In addition to the samples of DNA and cDNA derived from the different food matrices, a positive control which referred to a sample of DNA of the *Salmonella* serotype *Typhimurium* no. 75 obtained by boiling, and a negative control (NTC) in which water is added instead of sterile DNA, were also amplified.

Result

Both the positive controls and the negative controls gave expected results: the positive control gave a positive result and the result was negative in the negative control. Inhibition of PCR did not occur since amplification of the internal amplification control was obtained.

The results which were obtained after the real time PCR with the food matrices are shown in Table 5.

TABLE 5

Detection of DNA and RNA of *Salmonella* spp. by means of real time PCR and INVAVITWO probe in artificially contaminated food matrices.

| SAMPLE | DNA CHELEX EXTRACTION | RNA NUCLEOSPIN EXTRACTION |
|---|---|---|
| 1. Autoclaved chicken | + | + |
| 2. Autoclaved fish | + | + |
| 3. Autoclaved pastry | + | + |
| 4. TSB | + | + |

The invention claimed is:

1. An in vitro method for the detection of *Salmonella* spp. in a sample comprising
   (i) performing an amplification reaction using a nucleic acid preparation derived from said sample, a forward primer consisting of SEQ ID NO: 2, and a reverse primer consisting of SEQ ID NO: 3, wherein the primers are capable of amplifying the region of the *Salmonella* spp. invA gene comprised of the region between nucleotides 1001 and 1069 in SEQ ID NO: 1, and
   (ii) detecting the product of amplification generated in step (i).

2. The method according to claim 1, wherein the amplification reaction is a real time polymerase chain reaction.

3. The method according to claim 1, wherein the detection of the product of amplification is carried out by means of a fluorescent intercalating agent.

4. The method according to claim 1, wherein the detection of the product of amplification is carried out by means of a labeled probe.

5. The method according to claim 4, wherein the probe comprises a reporter pigment at its 5' end and a quencher pigment at its 3' end.

6. The method according to claim 4, wherein the probe comprises the nucleotide sequence shown in SEQ ID NO: 4.

7. The method according to claim 1, wherein the nucleic acid preparation comprises genomic DNA and/or cDNA obtained from RNA.

8. The method according to claim 1, wherein the sample is selected from the group consisting of an environmental sample, a clinical sample, and a food sample.

9. A combination of oligonucleotides comprising: a forward primer consisting of SEQ ID NO: 2, a reverse primer consisting of SEQ ID NO: 3, and a detection probe consisting of SEQ ID NO: 4, wherein the detection probe is labeled with a fluorescent dye.

10. A kit comprising a combination of oligonucleotides comprising: (a) a pair of primers specifically capable of amplifying the region of the *Salmonella* spp. invA gene comprised of the region between nucleotides 1001 and 1069 of SEQ ID NO: 1, wherein the pair of primers comprises a forward primer consisting of SEQ ID NO: 2 and a reverse primer consisting of SEQ ID NO: 3, and (b) an oligonucleotide detection probe that is labeled with a fluorescent dye and is capable of detecting the product of amplification generated by the pair of primers of (a).

11. The kit according to claim 10, wherein the probe further comprises a quencher pigment at its 3' end.

12. The kit according to claim 10, wherein the probe comprises the nucleotide sequence set forth in SEQ ID NO: 4.

13. The kit according to claim 12, further comprising a fluorescent intercalating agent.

* * * * *

SEQUENCE LISTING

<160> NUMBER OF SEQ ID NOS: 54

<210> SEQ ID NO 1
<211> LENGTH: 1950
<212> TYPE: DNA
<213> ORGANISM: Salmonella enterica

<400> SEQUENCE: 1

| | | | | | |
|---|---|---|---|---|---|
| aacagtgctc | gtttacgacc | cgaattactg | atcctggtac | taatggtgat | gatcatttct | 60 |
| atgttcgtca | ttccattacc | tacctatctg | gttgatttcc | tgatcgcgct | gaatatcgta | 120 |
| ctggcgatat | tggtgtttat | ggggtcgttc | tatattgaca | gaatcctcag | tttttcaacg | 180 |
| tttcctgcgg | tattgttaat | aacaacactc | tttcgtctgg | cattatcgat | cagtaccagc | 240 |
| cgtcttatct | tgatcgaggc | cgatgccggg | gaaattatcg | ccacgttcgg | gcaatttgtt | 300 |
| attggcgata | gcctggcggt | gggttttgtt | gtcttctcta | ttgtcactgt | ggttcagttt | 360 |
| atcgttatta | ccaaaggttc | agaacgcgtc | gcggaagtcg | cggcacgttt | ttctctggat | 420 |
| ggtatgcccg | gtaaacaaat | gagtatagat | gccgatttga | aggccggtat | tattgatgcg | 480 |
| gatgccgcac | gcgaacggcg | aagcgtactg | gaaagggaaa | gtcagcttta | cggttccttt | 540 |
| gacggtgcga | tgaagtttat | caaaggtgac | gccattgccg | gtatcattat | catctttgtg | 600 |
| aactttattg | gcggtatttc | ggtggggatg | acccgccatg | ggatggattt | atcctccgct | 660 |
| ctgtctactt | atactatgct | gaccatcggc | gatggtcttg | tcgcccagat | ccctgcactg | 720 |
| ttaattgcga | ttagtgccgg | ttttatcgtg | actcgcgtaa | atggcgatac | ggataatatg | 780 |
| ggccggaata | ttatgacgca | actgttgaac | aacccatttg | ttttggttgt | tacggctatt | 840 |
| ctgaccattt | caatgggaac | cctgccagga | tttccgctgc | cggtttttgt | cattctgtcg | 900 |
| gtggttttaa | gctactctt | ctattttaaa | ttccgtgaag | caaaacgtag | cgcaggcacg | 960 |
| cctaaaacca | gcaaaggcga | gcagccgctc | agtattgagg | aaaaggaagg | gacgtcgtta | 1020 |
| ggactgattg | gcgatctcga | taaagtttct | acagagaccg | taccactgat | attacttgtg | 1080 |
| ccgaagagtc | gacgtgaaga | tctggaaaaa | gcacagcttg | cggatcgtct | acgcagtcag | 1140 |
| ttctttattg | actatggtgt | gcgcctgccg | gaagtattgt | tacgcgatgg | tgaggggctg | 1200 |
| gacgataaca | gcattgtatt | gttgattaat | gagatccgtg | ttgaacaatt | tacggtctat | 1260 |
| tttgatttga | tgcgagtggt | aaattattcg | gatgaagtcg | tttcctttgg | cattaatcca | 1320 |
| actacccatc | agcaaggtag | cagtcagtat | ttctgggtga | cgcatgaaga | agggaaaag | 1380 |
| cttcgtgagc | ttggttatgt | gctgcggaac | gcgcttgacg | agctctacca | ctgtctggcg | 1440 |
| gtgacactgg | cgcgcaacgt | caatgaatat | ttcggtattc | aggaaacaaa | acatatgctg | 1500 |
| gatcagttgg | aggcaaaatt | tcctgattta | cttaaagaag | tgctcagaca | tgctaccgtg | 1560 |
| caacgtatat | cggaagtttt | gcagcgcctg | ttaagtgaac | gtgtttccgt | gcgtaatatg | 1620 |
| aaattaatta | tggaagcgct | cgcattatgg | gcgccaagag | aaaaagacgt | cattaacctg | 1680 |
| gtggaacata | ttcgtggagc | tatggcgcgt | tatatctgcc | ataaattcgc | caatggtggt | 1740 |
| gaattacgag | cagtaatggt | atctgctgaa | gttgaggatg | ttattcgcaa | agggatccgt | 1800 |
| cagacctctg | gcagtaccct | cctcagcctt | gaaccggaag | cctccgctaa | tttgatggat | 1860 |
| ctcattacac | ttaagctgga | tgatttattg | attgcacata | aagaccttgt | cctccttacg | 1920 |
| tctgtcgatg | tccgtcgatt | tattaagaaa | | | | 1950 |

<210> SEQ ID NO 2

```
<211> LENGTH: 21
<212> TYPE: DNA
<213> ORGANISM: Artificial Sequence
<220> FEATURE:
<223> OTHER INFORMATION: INVAVITWO forward primer

<400> SEQUENCE: 2
aaaggaaggg acgtcgttag g                                          21

<210> SEQ ID NO 3
<211> LENGTH: 24
<212> TYPE: DNA
<213> ORGANISM: Artificial Sequence
<220> FEATURE:
<223> OTHER INFORMATION: INVAVITWO reverse primer

<400> SEQUENCE: 3
cagtggtacg gtctctgtag aaac                                       24

<210> SEQ ID NO 4
<211> LENGTH: 15
<212> TYPE: DNA
<213> ORGANISM: Artificial Sequence
<220> FEATURE:
<223> OTHER INFORMATION: INVAVITWO probe

<400> SEQUENCE: 4
ctgattggcg atctc                                                 15

<210> SEQ ID NO 5
<211> LENGTH: 24
<212> TYPE: DNA
<213> ORGANISM: Artificial Sequence
<220> FEATURE:
<223> OTHER INFORMATION: INVAVITONE forward primer

<400> SEQUENCE: 5
ttaaattccg tgaagcaaaa cgta                                       24

<210> SEQ ID NO 6
<211> LENGTH: 18
<212> TYPE: DNA
<213> ORGANISM: Artificial Sequence
<220> FEATURE:
<223> OTHER INFORMATION: INVAVITONE reverse primer

<400> SEQUENCE: 6
aaccagcaaa ggcgagca                                              18

<210> SEQ ID NO 7
<211> LENGTH: 12
<212> TYPE: DNA
<213> ORGANISM: Artificial Sequence
<220> FEATURE:
<223> OTHER INFORMATION: INVAVITONE probe

<400> SEQUENCE: 7
cgcaggcacg cc                                                    12

<210> SEQ ID NO 8
<211> LENGTH: 46
<212> TYPE: DNA
<213> ORGANISM: Artificial Sequence
<220> FEATURE:
<223> OTHER INFORMATION: invA ICF primer

<400> SEQUENCE: 8
```

```
gtgaaattat cgccacgttc gggcaagcag aacgaaaaag gtgagc                  46
```

<210> SEQ ID NO 9
<211> LENGTH: 42
<212> TYPE: DNA
<213> ORGANISM: Artificial Sequence
<220> FEATURE:
<223> OTHER INFORMATION: invA ICR primer

<400> SEQUENCE: 9

```
tcatcgcacc gtcaaaggaa ccctgcactg ctcaatgcgc ca                      42
```

<210> SEQ ID NO 10
<211> LENGTH: 348
<212> TYPE: DNA
<213> ORGANISM: Artificial Sequence
<220> FEATURE:
<223> OTHER INFORMATION: 348 bp fragment of lambda phage amplified with
      the SEQ ID NO: 8 and SEQ ID NO: 9 primers

<400> SEQUENCE: 10

```
gtgaaattat cgccacgttc gggcaagcag aacgaaaaag gtgagccggt cacctggcag   60
gggcgacagt atcagccgta tcccattcag gggagcggtt ttgaactgaa tggcaaaggc  120
accagtacgc gccccacgct gacggtttct aacctgtacg gtatggtcac cgggatggcg  180
gaagatatgc agagtctggt cggcggaacg gtggtccggc gtaaggttta cgcccgtttt  240
ctggatgcgg tgaacttcgt caacggaaac agttacgccg atccggagca ggaggtgatc  300
agccgctggc gcattgagca gtgcagggtt cctttgacgg tgcgatga              348
```

<210> SEQ ID NO 11
<211> LENGTH: 38
<212> TYPE: DNA
<213> ORGANISM: Artificial Sequence
<220> FEATURE:
<223> OTHER INFORMATION: CI INVAVITWO forward primer

<400> SEQUENCE: 11

```
aaaggaaggg acgtcgttag ggtgcggtta tagcggtc                           38
```

<210> SEQ ID NO 12
<211> LENGTH: 41
<212> TYPE: DNA
<213> ORGANISM: Artificial Sequence
<220> FEATURE:
<223> OTHER INFORMATION: CI INVAVITWO reverse primer

<400> SEQUENCE: 12

```
tcagtggtac ggtctctgta gaaacttcgg aacttacaac c                       41
```

<210> SEQ ID NO 13
<211> LENGTH: 150
<212> TYPE: DNA
<213> ORGANISM: Artificial Sequence
<220> FEATURE:
<223> OTHER INFORMATION: 150 bp fragment of lambda phage amplified with
      the SEQ ID NO: 11 and SEQ ID NO: 12 primers

<400> SEQUENCE: 13

```
aaaggaaggg acgtcgttag ggtgcggtta tagcggtccg gctgtcgcgg atgaatatga   60
ccagccaacg tccgatatca cgaaggataa atgcagcaaa tgcctgagcg gttgtaagtt  120
ccgaagtttc tacagagacc gtaccactga                                   150
```

<210> SEQ ID NO 14

-continued

```
<211> LENGTH: 22
<212> TYPE: DNA
<213> ORGANISM: Artificial Sequence
<220> FEATURE:
<223> OTHER INFORMATION: probe used for detecting the product of
      amplification of the SEQ ID NO: 11 and SEQ ID NO: 12 primers

<400> SEQUENCE: 14
tgcggttata gcggtccggc tg                                            22

<210> SEQ ID NO 15
<211> LENGTH: 69
<212> TYPE: DNA
<213> ORGANISM: Salmonella spp.

<400> SEQUENCE: 15
aaaaggaagg gacgtcgtta ggactgattg gcgatctcga taaagtttct acagagaccg   60
taccactga                                                           69

<210> SEQ ID NO 16
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Enterica"
      /strain= "CNM-3685-03"

<400> SEQUENCE: 16
aaaaagaagg gtcgtcgtta ggactgattg gcgatctcga taaagtctct acagagaccg   60
taccgttga                                                           69

<210> SEQ ID NO 17
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Salamae"
      /strain= "CNM-5936-02"

<400> SEQUENCE: 17
aaaaagaggg gacatcgtta ggactgattg gcgatctcga taaagtttcc actgagactg   60
ttccattga                                                           69

<210> SEQ ID NO 18
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Salamae"
      /strain= "CNM-176"

<400> SEQUENCE: 18
aaaaagaggg gacgtcatta ggactgattg gcgatctcga taaagtctct acagagaccg   60
taccgttga                                                           69
```

```
<210> SEQ ID NO 19
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Salamae"
      /strain= "CNM-169"

<400> SEQUENCE: 19
aaaaagaagg gtcgtcgtta ggactgattg gcgatctcga taaagtctct acagagactg    60
taccgttga                                                            69

<210> SEQ ID NO 20
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Arizonae"
      /strain= "CNM-771-03"

<400> SEQUENCE: 20
aaaaggaagg gacgtcgtta ggactgattg gcgatctcga taaagtttct acagagaccg    60
taccactga                                                            69

<210> SEQ ID NO 21
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Arizonae"
      /strain= "CNM-247"

<400> SEQUENCE: 21
aaaaggaagg gacgtcgtta ggactgattg gcgatctcga taaagtttct acagagaccg    60
taccactga                                                            69

<210> SEQ ID NO 22
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Arizonae"
      /strain= "CNM-259"

<400> SEQUENCE: 22
aaaaggaagg gacgtcgtta ggactgattg gcgatctcga taaagtttct acagagaccg    60
taccactga                                                            69

<210> SEQ ID NO 23
<211> LENGTH: 69
<212> TYPE: DNA
```

```
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Diarizonae"
      /strain= "CNM-834-02"

<400> SEQUENCE: 23
aaaaagaagg gacgtcgtta ggactgattg gcgatctcga taaagtctct acagagaccg    60
taccgttga                                                           69

<210> SEQ ID NO 24
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Diarizonae"
      /strain= "CNM-750-02"

<400> SEQUENCE: 24
aaaaagaagg gacgtcgtta ggactgattg gcgatctcga taaagtctct acagagaccg    60
taccgttga                                                           69

<210> SEQ ID NO 25
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Diarizonae"
      /strain= "CNM-2667-02"

<400> SEQUENCE: 25
aaaaagaagg gacgtcgtta ggactgattg gcgatctcga taaagtctct acagagaccg    60
taccgttga                                                           69

<210> SEQ ID NO 26
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Houtenae"
      /strain= "ST-22"

<400> SEQUENCE: 26
aaaaagaagg gtcgtcgttg ggactgattg gcgatctcga taaagtctct acagagaccg    60
taccgttga                                                           69

<210> SEQ ID NO 27
<211> LENGTH: 69
<212> TYPE: DNA
<213> ORGANISM: Salmonella enterica
<220> FEATURE:
<221> NAME/KEY: source
<222> LOCATION: (1)..(69)
```

```
<223> OTHER INFORMATION: /organism= "Salmonella enterica"
     /mol_type= "DNA"
     /subsp.= "Indica"
     /strain= "CNM-186"

<400> SEQUENCE: 27
aaaaagaggg gacatcgtta ggactgattg gcgatctcga taaagtttcc actgagactg    60
ttccattga                                                           69

<210> SEQ ID NO 28
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
     /mol_type= "DNA"
     /subsp.= "Indica"
     /strain= "CDC-811"

<400> SEQUENCE: 28
aaaaagaagg aacgtcgcta ggactgattg gcgatctcga taaagtctct acagagaccg    60
tacctttga                                                           69

<210> SEQ ID NO 29
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
     /mol_type= "DNA"
     /subsp.= "Indica"
     /strain= "CDC-1937"

<400> SEQUENCE: 29
aaaaagaagg aacgtcgtta ggactgattg gcgatctcga taaagtctct acagagaccg    60
tacctttga                                                           69

<210> SEQ ID NO 30
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
     /mol_type= "DNA"
     /strain= "RKS4194"

<400> SEQUENCE: 30
aaaaagaagg gtcgtcgtta ggactgattg gcgatctcga taaagtctct acagagaccg    60
taccgttga                                                           69

<210> SEQ ID NO 31
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
     /mol_type= "DNA"
     /strain= "RKS3333"

<400> SEQUENCE: 31
```

-continued

```
aaaaagaagg gtcgtcgtta ggactgattg gcgatctcga taaagtctct acagagactg    60
taccgttga                                                            69
```

<210> SEQ ID NO 32
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS3057"

<400> SEQUENCE: 32

```
aaaaagaggg gacgtcatta ggactgattg gcgatctcga taaagtctct acagagaccg    60
taccgttga                                                            69
```

<210> SEQ ID NO 33
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS3044"

<400> SEQUENCE: 33

```
aaaaagaggg gacatcgtta ggactgattg gcgatctcga taaagtttcc actgagactg    60
ttccattga                                                            69
```

<210> SEQ ID NO 34
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS3041"

<400> SEQUENCE: 34

```
aaaaagaggg gacatcgtta ggactgattg gcgatctcga taaagtttcc actgagactg    60
ttccattga                                                            69
```

<210> SEQ ID NO 35
<211> LENGTH: 69
<212> TYPE: DNA
<213> ORGANISM: Salmonella enterica invasion
<220> FEATURE:
<221> NAME/KEY: source
<222> LOCATION: (1)..(69)
<223> OTHER INFORMATION: /organism= "Salmonella enterica invasion"
      /mol_type= "DNA"
      /strain= "RKS3027"

<400> SEQUENCE: 35

```
aaaaagaagg aacgtcgtta ggactgattg gcgatctcga taaagtctct acagagaccg    60
taccttga                                                             69
```

<210> SEQ ID NO 36
<211> LENGTH: 69

```
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS3015"

<400> SEQUENCE: 36
aaaaagaagg aacgtcgcta ggactgattg gcgatctcga taaagtctct acagagaccg      60
tacctttga                                                             69

<210> SEQ ID NO 37
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS3014"

<400> SEQUENCE: 37
aaaaagaagg aacgtcgcta ggactgattg gcgatctcga taaagtctct acagagaccg      60
tacctttga                                                             69

<210> SEQ ID NO 38
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS3013"

<400> SEQUENCE: 38
aaaaagaagg aacgtcgcta ggactgattg gcgatctcga taaagtctct acagagaccg      60
tacctttga                                                             69

<210> SEQ ID NO 39
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2995"

<400> SEQUENCE: 39
aaaaagaggg gacgtcatta ggactgattg gcgatctcga taaagtctct acagagaccg      60
taccgttga                                                             69

<210> SEQ ID NO 40
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2993"
```

```
<400> SEQUENCE: 40
aaaaagaagg gacgtcgtta ggactgattg gcgacctcga taaagtctct acagagaccg      60
taccgttga                                                              69

<210> SEQ ID NO 41
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2985"

<400> SEQUENCE: 41
aaaaagaagg gacgtcgtta ggactgattg gcgacctcga taaagtctct acagagaccg      60
taccgttga                                                              69

<210> SEQ ID NO 42
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2983"

<400> SEQUENCE: 42
aaaaggaagg gacgtcgtta ggactgattg gcgatctcga taaagtttct acagagaccg      60
taccactga                                                              69

<210> SEQ ID NO 43
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2980"

<400> SEQUENCE: 43
aaaaggaagg gacgtcgtta ggactgattg gcgatctcga taaagtttct acagagaccg      60
taccactga                                                              69

<210> SEQ ID NO 44
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2979"

<400> SEQUENCE: 44
aaaaagaagg gacgtcgtta ggactgattg gcgatctcga taaagtctct acagagaccg      60
taccgttga                                                              69
```

```
<210> SEQ ID NO 45
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS2978"

<400> SEQUENCE: 45
aaaaagaagg gacgtcgtta ggactgattg gcgatctcga taaagtctct acagagaccg    60
taccgttga                                                            69

<210> SEQ ID NO 46
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS1280"

<400> SEQUENCE: 46
aaaaagaagg gtcgtcgtta ggactgattg gcgatctcga taaagtctct acagagactg    60
taccgttga                                                            69

<210> SEQ ID NO 47
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /strain= "RKS1518"

<400> SEQUENCE: 47
aaaaagaagg gtcgtcgttg ggactgattg gcgatctcga taaagtctct acagagaccg    60
taccgttga                                                            69

<210> SEQ ID NO 48
<211> LENGTH: 69
<212> TYPE: DNA
<213> ORGANISM: Salmonella gallinarum
<220> FEATURE:
<221> NAME/KEY: source
<222> LOCATION: (1)..(69)
<223> OTHER INFORMATION: /organism= "Salmonella gallinarum"
      /mol_type= "DNA"
      /strain= "RKS2962"

<400> SEQUENCE: 48
aaaaagaagg gtcgtcgttg ggactgattg gcgatctcga taaagtctct acagagaccg    60
taccgttga                                                            69

<210> SEQ ID NO 49
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
```

-continued

```
        /mol_type= "DNA"
        /subsp.= "Arizonae"
        /strain= "CNM-822-02"

<400> SEQUENCE: 49
aaaaggaagg gacgtcgtta ggactgattg gcgatctcga taaagtttct acagagaccg      60
taccactga                                                             69

<210> SEQ ID NO 50
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
        /mol_type= "DNA"
        /subsp.= "Houtenae"
        /strain= "CNM-2556-03"

<400> SEQUENCE: 50
aaaaagaagg aacgtcgtta ggactgattg gcgatctcga taaagtctct acagagaccg      60
tacctttga                                                             69

<210> SEQ ID NO 51
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
        /mol_type= "DNA"
        /subsp.= "Houtenae"
        /strain= "ST-15"

<400> SEQUENCE: 51
aaaaagaagg aacgtcgcta ggactgattg gcgatctcga taaagtctct acagagaccg      60
tacctttga                                                             69

<210> SEQ ID NO 52
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
        /mol_type= "DNA"
        /subsp.= "Enterica"
        /serovar= "Gallinarum"
        /strain= "S9873"

<400> SEQUENCE: 52
aaaaagaagg gtcgtcgtta ggactgattg gcgatctcga taaagtctct acagagaccg      60
taccgttga                                                             69

<210> SEQ ID NO 53
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
        /mol_type= "DNA"
        /subsp.= "Enterica"
        /serovar= "Pullorum"
```

```
/strain= "1794"

<400> SEQUENCE: 53
aaaaagaagg gtcgtcgtta ggactgattg gcgatctcga taaagtctct acagagaccg      60
taccgttga                                                              69

<210> SEQ ID NO 54
<211> LENGTH: 69
<212> TYPE: DNA
<213> ORGANISM: Salmonella enterica
<220> FEATURE:
<221> NAME/KEY: source
<222> LOCATION: (1)..(69)
<223> OTHER INFORMATION: /organism= "Salmonella enterica"
      /mol_type= "DNA"
      /subsp.= "Enterica"
      /serovar= "Senftenberg"
      /strain= "JXS-04#01"

<400> SEQUENCE: 54
aaaaagaagg gtcgtcgtta ggactgattg gcgatctcga taaagtctct acagagactg      60
taccgttga                                                              69
```